(12) United States Patent
Wakayama et al.

(10) Patent No.: US 11,911,417 B2
(45) Date of Patent: Feb. 27, 2024

(54) NERVE GROWTH PROMOTER AND METHOD FOR PRODUCING SAME, INTERNAL PREPARATION, MEDIUM ADDITIVE, CELL DILUTION ADDITIVE, MEDIUM, CELL DILUTION, ANTIOXIDANT AND METHOD FOR PRODUCING SAME, EXTERNAL PREPARATION, AND WOUND TREATMENT AGENT AND METHOD FOR PRODUCING SAME

(71) Applicant: LAIMU CORPORATION, Yokohama (JP)

(72) Inventors: Sachio Wakayama, Yokohama (JP); Akihiro Tai, Shobara (JP)

(73) Assignee: LAIMU CORPORATION, Kanagawa (JP)

(*) Notice: Subject to any disclaimer, the term of this patent is extended or adjusted under 35 U.S.C. 154(b) by 528 days.

(21) Appl. No.: 17/194,625

(22) Filed: Mar. 8, 2021

(65) Prior Publication Data
US 2021/0187041 A1    Jun. 24, 2021

Related U.S. Application Data

(62) Division of application No. 16/076,780, filed as application No. PCT/JP2017/004863 on Feb. 10, 2017, now Pat. No. 10,973,858.

(30) Foreign Application Priority Data

Feb. 12, 2016   (JP) .................................. 2016-024655
Feb. 12, 2016   (JP) .................................. 2016-024656
Feb. 12, 2016   (JP) .................................. 2016-024657

(51) Int. Cl.
| | | |
|---|---|---|
| *A61K 35/57* | (2015.01) | |
| *A23L 3/3526* | (2006.01) | |
| *A23L 3/3562* | (2006.01) | |
| *A61K 38/00* | (2006.01) | |
| *A61K 8/64* | (2006.01) | |
| *A61Q 19/08* | (2006.01) | |
| *A61K 31/728* | (2006.01) | |
| *A61K 8/73* | (2006.01) | |
| *C09K 15/34* | (2006.01) | |
| *A61K 8/98* | (2006.01) | |
| *A61P 17/02* | (2006.01) | |
| *A61P 25/00* | (2006.01) | |

(52) U.S. Cl.
CPC ............ *A61K 35/57* (2013.01); *A23L 3/3526* (2013.01); *A23L 3/3562* (2013.01); *A61K 8/64* (2013.01); *A61K 8/73* (2013.01); *A61K 8/735* (2013.01); *A61K 8/98* (2013.01); *A61K 8/981* (2013.01); *A61K 31/728* (2013.01); *A61K 38/00* (2013.01); *A61P 17/02* (2018.01); *A61P 25/00* (2018.01); *A61Q 19/08* (2013.01); *C09K 15/34* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,713,448 A | 12/1987 | Balazs | |
| 4,736,024 A | 4/1988 | Della Valle et al. | |
| 2002/0133033 A1 | 9/2002 | Beaudoin et al. | |
| 2016/0068499 A1 | 3/2016 | Reddell | |

FOREIGN PATENT DOCUMENTS

| | | |
|---|---|---|
| CN | 1794999 A | 6/2006 |
| EP | 1 611 893 A1 | 1/2006 |
| EP | 2 818 172 A1 | 12/2014 |
| EP | 2 818 543 A1 | 12/2014 |
| JP | 09-30979 A | 7/1995 |
| JP | 2001-178406 A | 7/2001 |
| JP | 2002-145800 A | 5/2002 |
| JP | 2002-356432 A | 12/2002 |
| JP | 2008 029354 A | 2/2008 |
| JP | 2008-511613 A | 4/2008 |
| JP | 2009-22206 A | 2/2009 |
| JP | 2009-079043 A | 4/2009 |
| JP | 2010-99001 A | 5/2010 |
| JP | 2014-129368 A | 7/2014 |
| JP | 2015 040173 A | 3/2015 |
| JP | 2015-40173 A | 3/2015 |
| WO | 2006/25068 A1 | 3/2006 |
| WO | 2013/125634 A | 8/2013 |

OTHER PUBLICATIONS

Office Action dated Apr. 16, 2021 issued in the corresponding Chinese patent application No. 201780010220.4 with its English Machine Translation.
Notice of Reexamination dated Nov. 14, 2022 issued in the corresponding Chinese patent application No. 201780010220.4 with its English Machine Translation.
Li Dongguang (Ed.), "Formulation and Process of Fine Chemical Products 2", chemical Industry Press, Jan. 2001, the first edition, the first printing, pp. 202-203, published on Jan. 31, 2001.
Chen Wei, "The attending physician in Department of Nutrition of Peking Union Medical College Hospital to tell you to choose nutritional health products scientifically", china Light Industry Press, Jul. 2007, 1st edition, 1st printing, p. 54, published on Jul. 31, 2007.
Decision of reexamination dated Jun. 9, 2023 issued in the corresponding Chinese patent application No. 201780010220.4 with its English Machine Translation.

(Continued)

*Primary Examiner* — Terry A McKelvey
*Assistant Examiner* — Jacob A Boeckelman
(74) *Attorney, Agent, or Firm* — BROWDY AND NEIMARK, PLLC

(57) ABSTRACT

A nerve growth promoter and an antioxidant containing a degradation product obtained by degrading a composition containing a hyaluronic acid and a protein with a protease. A would treatment agent containing an ethyl acetate extract of a degradation product obtained by degrading a composition containing a hyaluronic acid and a protein with a protease.

2 Claims, 9 Drawing Sheets

(56) References Cited

OTHER PUBLICATIONS

Dou Dediang (editor), chemistry of Traditional Chinese Medicine, hunan Science and Technology Press, Apr. 2012, the first edition, the first printing, p. 13.
Extended European search report dated Mar. 9, 2023, from corresponding European patent application No. 22210283.2.
Notification of Reexamination dated Mar. 10, 2023, from corresponding Chinese patent application No. 201780010220.4.
Torigoe, et al., Hyaluronan tetrasaccharide promotes regeneration of peripheral nerve: in vivo analysis by film model method, Brain Research, 1385:87-92 (2011).
International Search Report and Written Opinion for corresponding PCT International Application No. PCT/JP2017/004863.
International Preliminary Report on Patentability for corresponding PCT International Application No. PCT/JP2017/004863, dated Aug. 23, 2018, with English translation.
Office Action dated Nov. 21, 2017 with its English Machine Translation issued in corresponding Japanese patent application No. 2016-024655.
Office Action dated May 15, 2018 with its English Machine Translation issued in corresponding Japanese patent application No. 2016-024655
Office Action dated Jul. 31, 2018 with its English Machine Translation issued in corresponding Japanese patent application No. 2016-024655.
Office Action dated May 9, 2017 with its English Machine Translation issued in the corresponding Japanese patent application No. 2016-024657.
Office Action dated Aug. 15, 2017, issued in the corresponding Japanese patent application No. 2016-024657.
Okinawa industrial-arts center research report No. 11, 2008, the 1-5th page.
Lima et al., Taurine-induced regeneration of goldfish retina in culture may involve a calcium-mediated mechanism, Journal of Neurochemistry, 1993, and vol. 60, No. 6 and pp. 2153-2158.
Mitoma et al., A novel metabolic communication between neurons and astrocytes: non-essential amino acid L-serine released from astrocytes is essential for developing hippocampal neurons, Neuroscience Research, 1998, vol. 30, pp. 195-199.
Hartwig et al., Elevated phenylalnine levels interfere with neurite outgrowth stimulated by the neuronal cell adhesion molecule L1 in vitro, FEBS Letters, 2006, vol. 580, pp. 3489-3492.
Office Action dated Jul. 23, 2019 issued in the corresponding Japanese patent application No. 2016-024655 with its English Machine Translation.
Extended European Search Report dated Sep. 6, 2019 issued in the corresponding European patent application No. 17750347.1.
Office Action dated Jan. 16, 2020, in corresponding Chinese patent application No. 201780010220.4 with English machine translation.
Office Action dated Sep. 15, 2020, issued in corresponding Chinese patent application No. 201780010220.4 with its Partial English Translation
Yu Bangchao et al., "Enzyme Engineering (Third Edition)", pp. 196-197, Central China Normal University Press, 2014. 1.
Kreuger et al., Effects of the topical application of an ethyl acetate fraction from Vemonia scorpioides on excisional wounds infected with *Staphylococcus aureus* in rats, Brazilian Journal of Pharmacognosy 22(1): 123-130, 2012 (Year: 2012).
Gothai et al., Wound healing properties of ethyl acetate fraction of Moringa oleifera in normal human dermal fibroblasts, J Intercult Ethnopharmacol, vol. 5, Issue 1, Feb. 8, 2016 (Year: 2016).
Boas et al., Isolation of hyaluronic acid from the cock's comb, J. Biol. Chem, 181 :573-575, 1949 (Year: 1949).
Rosa et al., Purification and characterization of hyaluronic acid from chicken combs, Ciencia Rural, Santa Maria, v. 42, n.9, p. 1682-1687, 2012 (Year: 2012).
Sarker et al., Chapters 1 and 2, Natural Products Isolation, Methods and Protocols, Third edition, 2012) (Year: 2012).

[FIG. 1]
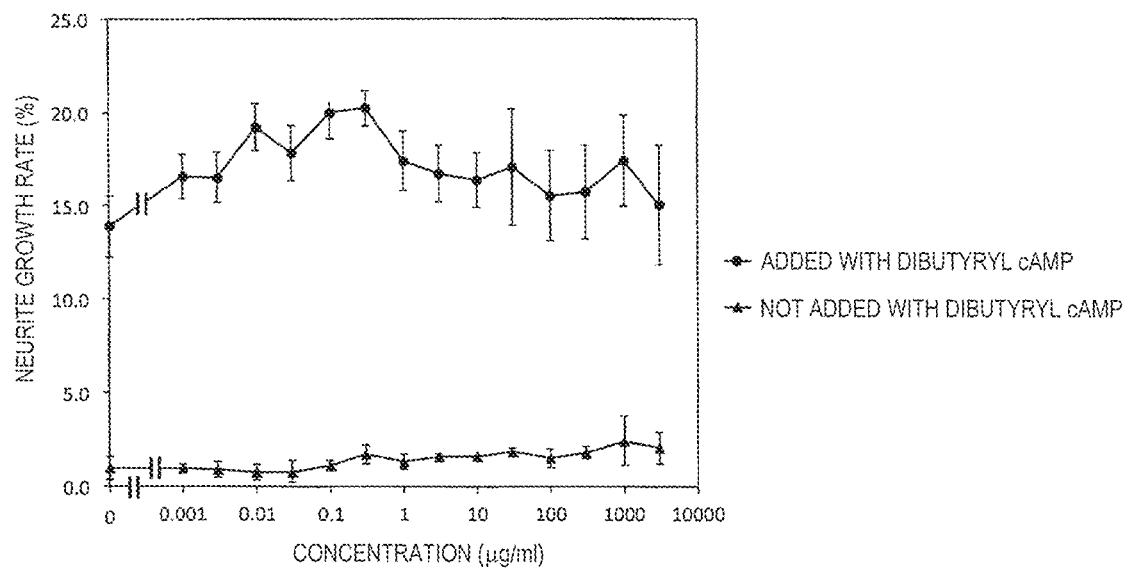
[FIG. 2]
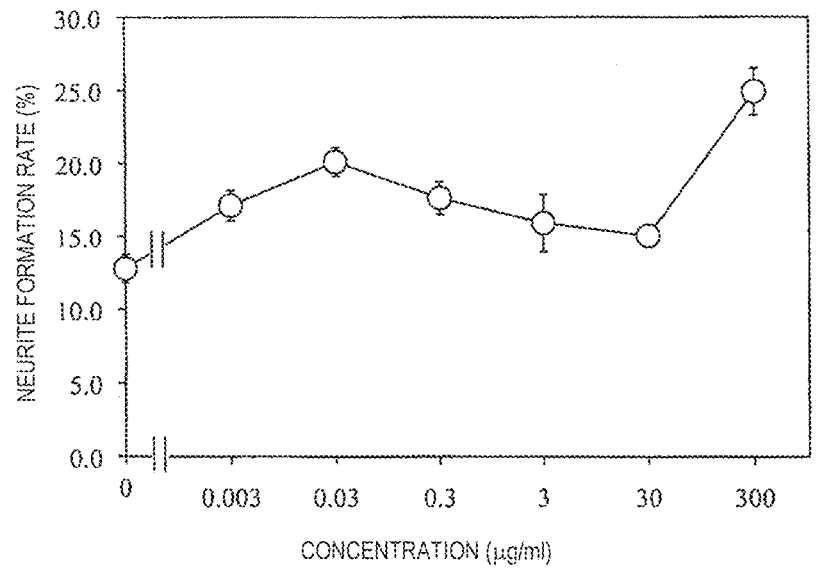

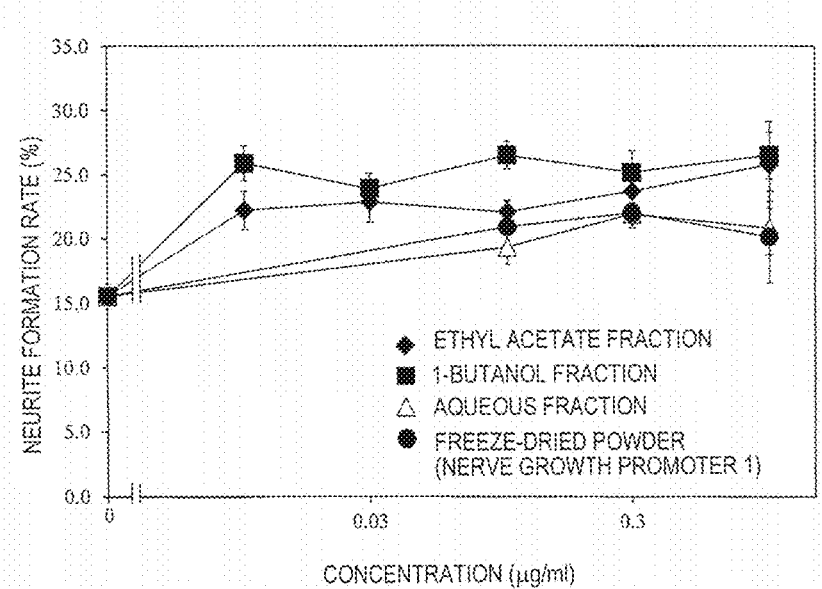
[FIG. 3]

[FIG. 4]
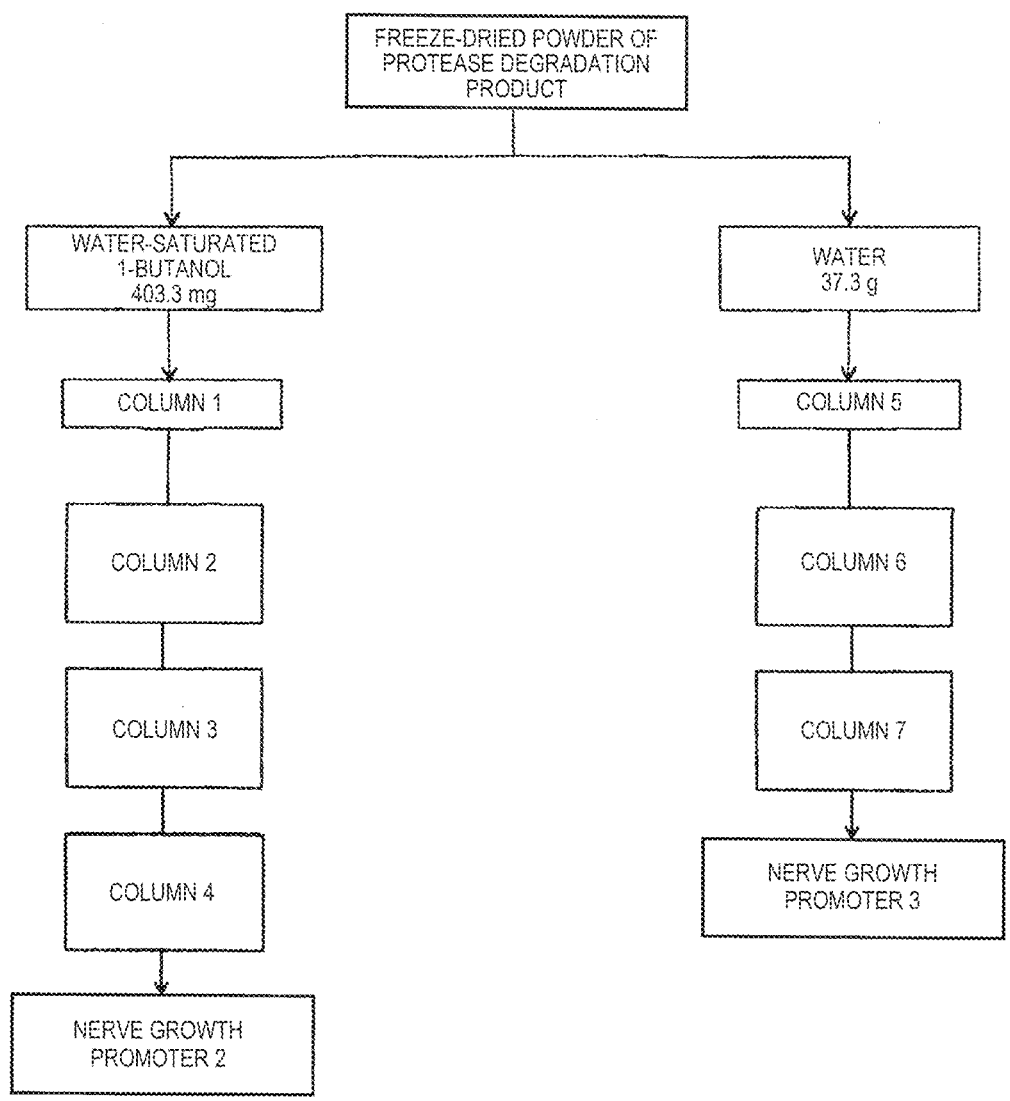

[FIG. 5]
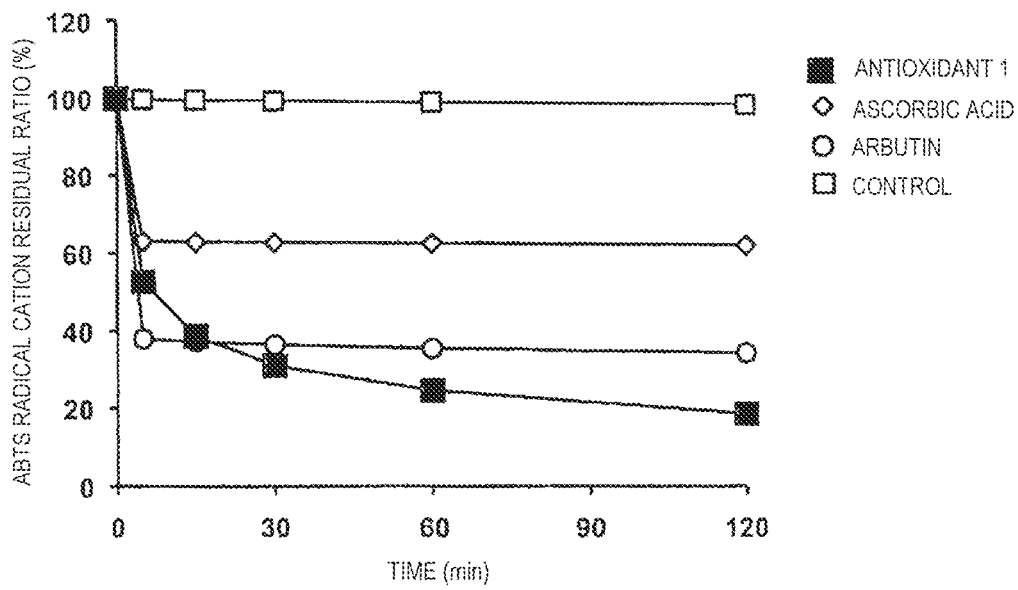
[FIG. 6]
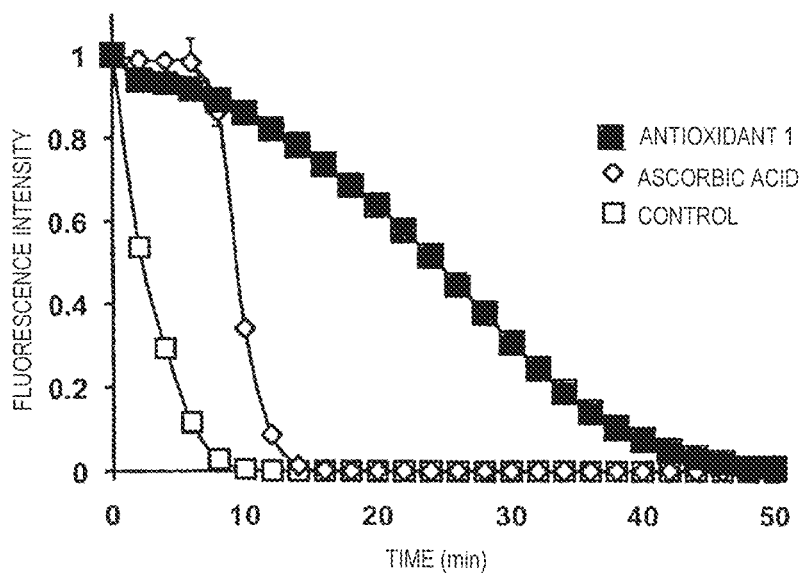

[FIG. 7]
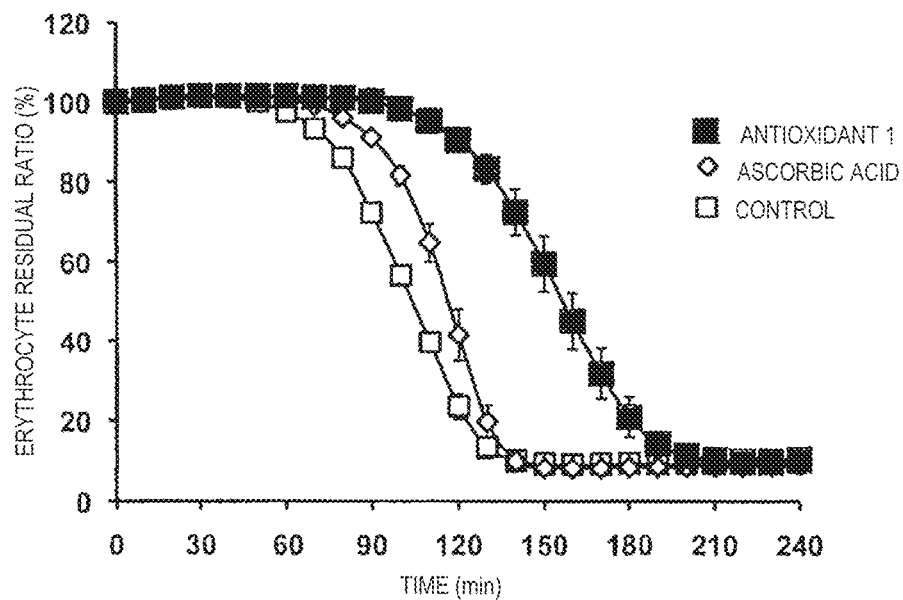
[FIG. 8]
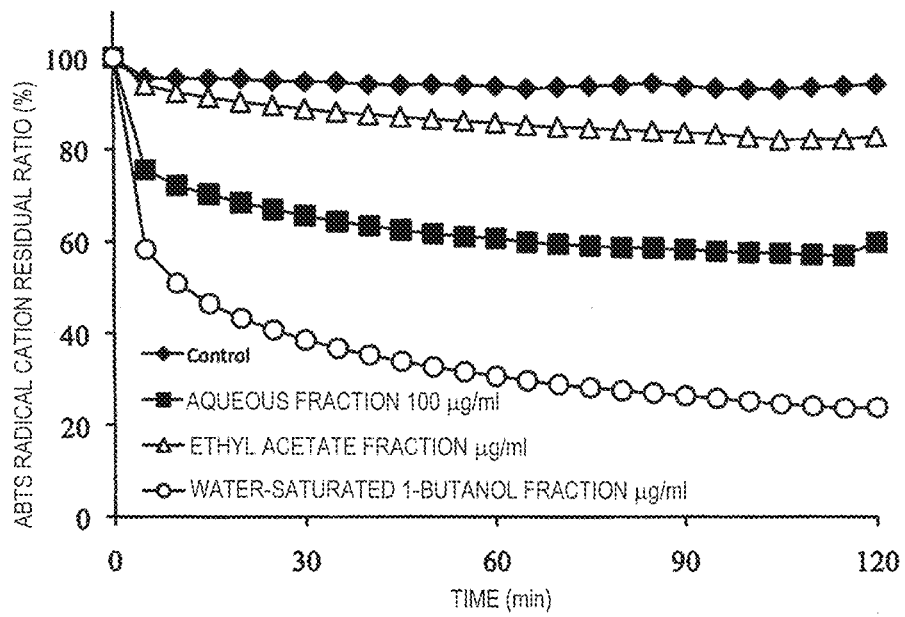

[FIG. 9]
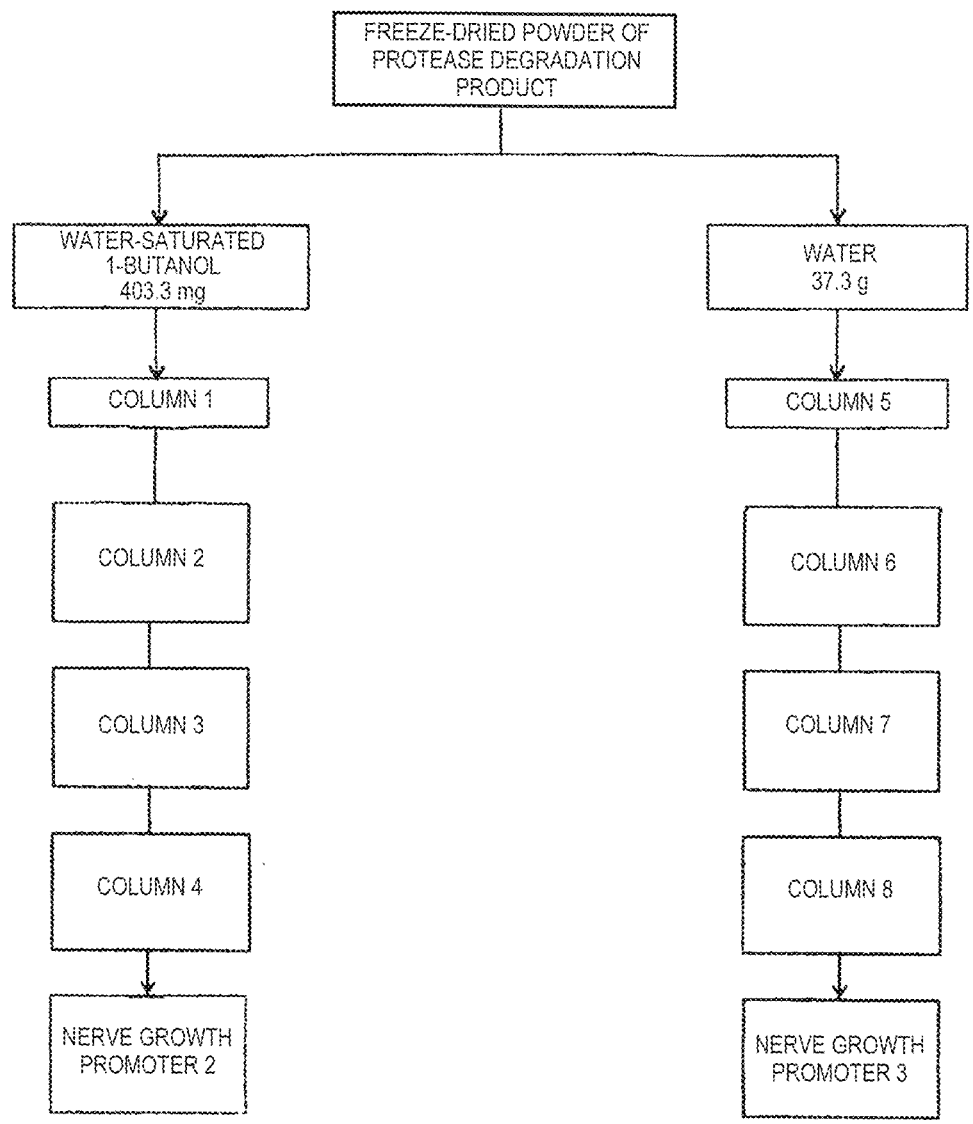

[FIG. 10]
(a)
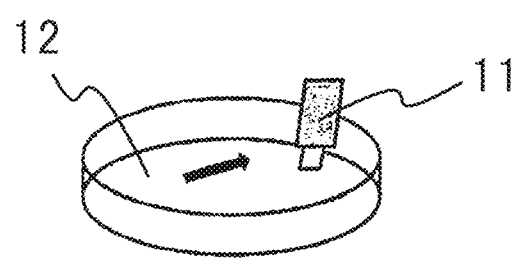
(b)
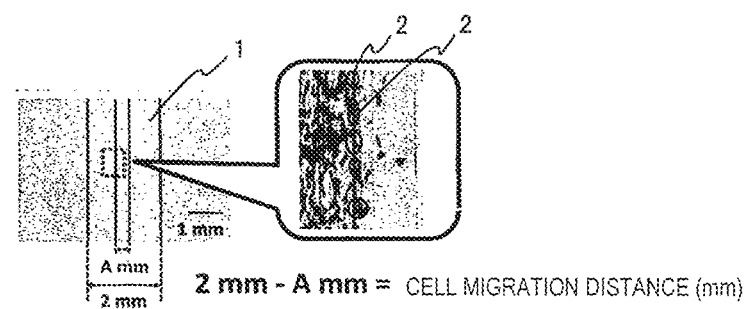
2 mm − A mm = CELL MIGRATION DISTANCE (mm)

[FIG. 11]
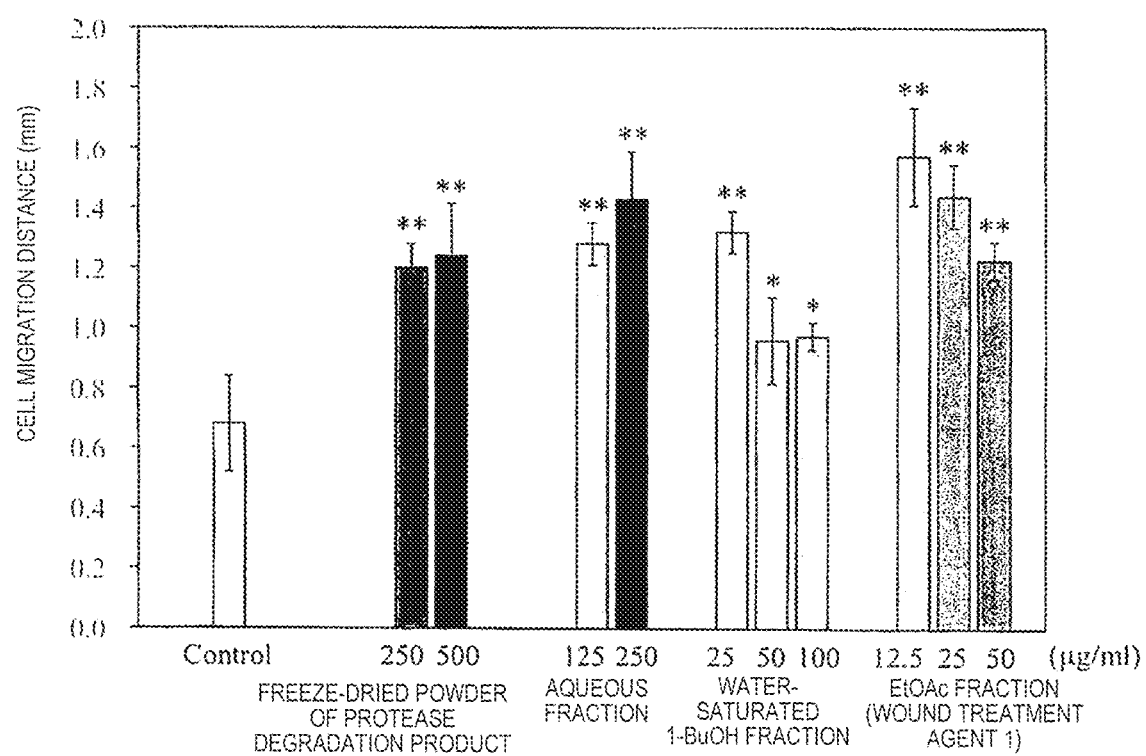

[FIG. 12]
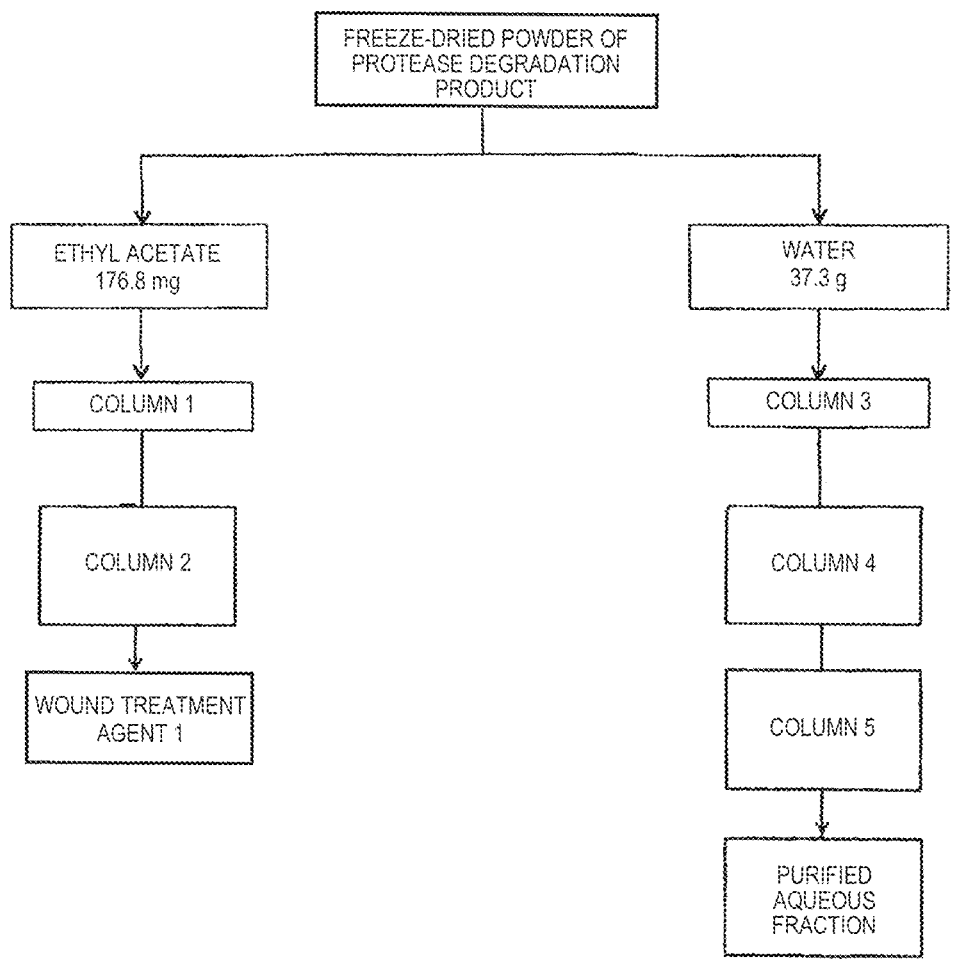

NERVE GROWTH PROMOTER AND METHOD FOR PRODUCING SAME, INTERNAL PREPARATION, MEDIUM ADDITIVE, CELL DILUTION ADDITIVE, MEDIUM, CELL DILUTION, ANTIOXIDANT AND METHOD FOR PRODUCING SAME, EXTERNAL PREPARATION, AND WOUND TREATMENT AGENT AND METHOD FOR PRODUCING SAME

TECHNICAL FIELD

The present invention relates to a nerve growth promoter, an antioxidant, a wound treatment agent, and methods for producing them. The present invention also relates to an internal preparation, an external preparation, a medium additive, a cell dilution additive, a medium, and a cell dilution.

BACKGROUND ART

Hyaluronic acid is known to have an action of enhancing a moisturizing effect and a water-retentive effect, and has heretofore been incorporated in various cosmetics and medicines. For example, hyaluronic acid is generally used by directly applying it to a dry skin or a rough skin so as to enhance the moisture-retaining property thereof for skin conditioning, or for preventing moisture from being lost from the skin surface in a dry season, hyaluronic acid is preventively applied to the skin surface. In addition, hyaluronic acid is expected to express a function derived from the moisturizing effect thereof or any other useful characteristics than the moisturizing effect, and some studies are known relating to new use thereof.

For example, PTL 1 proposes use of a degradation product produced by degrading a composition containing a hyaluronic acid and a protein with a protease, as a wound treatment agent. The wound treatment agent uses a hyaluronic acid and a protein that are biogenic substances, and a slow-reacting enzyme, and is therefore highly safe, and can quickly treat a wound, for example, through oral administration or direct administration to a region of wound.

CITATION LIST

Patent Literature

PTL 1: JP-2002-145800A

SUMMARY OF INVENTION

Technical Problem

As described above, a degradation product produced by degrading a composition containing a hyaluronic acid and a protein with a protease is highly useful as a wound treatment agent. However, the degradation product has been merely confirmed to have a wound treatment effect but any other effect thereof is almost unknown, and the application range of the product is limited.

(1) On the other hand, as human disorders that have extremely serious influences on daily life, there are known neurodegenerative diseases such as Parkinson's disease and Alzheimer's disease, and nerve damages caused by cerebral ischemia, cerebral contusion or spinal cord injury. By such nerve disorders, cognitive function for comprehension, memory and judgement as well as motor function may be damaged, and it would become difficult to continue normal life, drastically changing from life forever. Consequently, development of medicines and medical technologies for relieving such nerve system function disorders is strongly desired.

Here, the cognitive function and the motor function in animals such as human beings are enabled by the complicated nerve circuits that are formed by the cell bodies of neuron cells to elongate the neurites to mutually construct synapses, and it is known that in many nerve disorders, the neurites to form nerve circuits are denatured or dropped off in the early stage. Consequently, for restraining the progress of nerve disorders or for relieving the symptoms thereof, it is considered that suppression of neurite denaturation or administration of a substance capable of promoting formation or growth of neurites for the purpose of complementing the denatured or dropped neurites would be effective. On the other hand, for recovering the cognitive function and the motor function damaged by nerve damage, it also is considered that administration of a substance capable of promoting the formation and growth of neurites to reconstruct nerve circuits would be effective. From these points, recently, development of a substance that forms and elongates neurites has become actively made and many reports have been made. However, the situation is such that the substance that has heretofore been reported to promote the formation and growth of neurites is hardly available or is unsuitable for internal use or the effect thereof is insufficient, and a nerve growth promoter that exhibits a high effect and is inexpensive and suitable for internal use is not as yet realized.

For solving the problems in the existing technology, the present inventors have promoted investigations for the purpose of providing a nerve growth promoter that exhibits a high effect of promoting formation and growth of neurites and is suitable for internal use. In addition, the inventors have further promoted investigations for providing a method for producing a nerve growth promoter capable of producing such a nerve growth promoter at low cost.

(2) On the other hand, recently, a negative influence of active oxygen generated in a living organism on the living organism has become a big problem. Active oxygen means an oxygen molecule having a higher activity than an ordinary oxygen molecule and a related substance thereof, including active oxygen in the narrow sense such as super oxide ($\cdot O_2^-$), hydroxyl radical ($HO\cdot$), hydrogen peroxide ($H_2O_2$), and singlet oxygen ($^1O_2$), and in addition thereto, further including radical species such as a hydroperoxyl radical, an alkoxyl radical, and an alkylperoxyl radical, and non-radical species such as a peroxy nitride, and a lipid hydroperoxide. The active oxygen in the narrow sense is generated in a process where a living organism consumes oxygen ($^3O_2$), and when such an active oxygen is generated excessively, important biogenic substances such as DNA, lipid, enzyme and protein are oxidized by the active oxygen to cause so-called oxygenation failures to form other active oxygen or oxidized denatured products. Such oxygenation failure caused by active oxygen is known to promote an aging phenomenon, and has been clarified to deeply relate to development of various diseases including adult lifestyle-related diseases such as diabetes, hypertension and arteriosclerosis.

As a method for preventing oxygenation failures of a living organism to be caused by active oxygen, a method of administering an antioxidant to a living organism to remove the active oxygen. The antioxidant includes a water-soluble antioxidant such as flavonoid, catechin and vitamin C (ascorbic acid), and a fat-soluble antioxidant such as vitamin E and p-carotene. The fat-soluble antioxidant accumulates in the body and is therefore problematic in that selection of the dose and the administration method thereof is difficult. On the other hand, the water-soluble antioxidant does not cause such a problem of accumulation in the body, and is therefore much used as supplements in addition to medicines, but a high antioxidation activity thereof capable of fully preventing the oxygenation failures in a living organism is not recognized.

Given the situation, for the purpose of solving the problems in the existing technology, the present inventors have made further investigations so as to provide an antioxidant having a high antioxidation activity and capable of effectively preventing oxygenation failures of biogenic substances, and a method for producing such an antioxidant.

(3) As described above, a degradation product produced by degrading a composition containing a hyaluronic acid and a protein with a protease is known to be highly useful as a wound treatment agent. However, when the present inventors tried the degradation product to evaluate the wound healing promoting effect thereof based on the migration range of human skin fibroblasts at a region of wound, and have found that, in order to attain a significant wound healing promoting effect for the evaluation, a relatively high concentration of the degradation product need to be administered. When a high concentration of a degradation product is incorporated in a wound treatment agent, combined use with any other component and mixing with a vehicle may be greatly restricted, and further improvement is considered to be necessary.

Given the situation, the present inventors have further made various investigations for enhancing the wound healing promoting effect of the degradation product, and during the course thereof, the inventors have made other investigations of processing the degradation product for liquid-liquid separation using various solvents followed by evaluating the wound healing promoting effect of the each of the resultant fractions. As a result, the present inventors have found for the first time that the wound healing promoting effect of each fraction of the degradation product significantly differs depending on the type and the combination of the solvents used for liquid-liquid separation.

Under the situation, the present inventors have further made assiduous investigations, aiming at a technical theme of providing a wound treatment agent using a degradation product produced by degrading a composition containing a hyaluronic acid and a protein with a protease, which can attain a high wound healing promoting effect even though the concentration of the degradation product product is low, and providing a method for producing the wound treatment agent.

Solution to Problem

The present inventors have made assiduous studies for the purpose of solving the above-mentioned problems (1) to (3) and, as a result, have found for the first time that a degradation product produced by degrading the above-mentioned composition known to have a wound healing effect, that is, the composition containing a hyaluronic acid and a protein, with a protease has a strong nerve growth promoting effect and an antioxidant effect. With that, the present inventors have further found that, utilizing the nerve growth promoting effect of the degradation product, a nerve growth promoter suitable for internal use and an antioxidant suitable for internal use and external use can be provided at low cost.

Further, the present inventors have found that an ethyl acetate fraction obtained through liquid-liquid separation of the degradation product produced by degrading the composition containing a hyaluronic acid and a protein with a protease, with ethyl acetate and water has an extremely high wound healing promoting effect. Specifically, the inventors have obtained a knowledge that the ethyl acetate fraction can exhibit a wound healing promoting effect higher than the effect recognized by the degradation product even when the concentration of the fraction corresponds to $\frac{1}{10}$ or less of the concentration of the degradation product recognized to exhibit a wound healing promoting effect.

The present invention has been proposed based on these findings, and specifically has the following constitution.

[1] A nerve growth promoter containing a degradation product obtained by degrading a composition containing a hyaluronic acid and a protein with a protease.

[2] The nerve growth promoter according to [1], wherein the composition is a comb.

[3] The nerve growth promoter according to [1] or [2], wherein the degradation product contains a low-molecular hyaluronic acid having a molecular weight of 380 to 5000.

[4] The nerve growth promoter according to any one of [1] to [3], wherein the content of the low-molecular hyaluronic acid having a molecular weight of 380 to 5000 is 10% by mass or more relative to the total amount of the nerve growth promoter.

[5] The nerve growth promoter according to [3] or [4], wherein the proportion of a low-molecular hyaluronic acid having a molecular weight of 1520 to 5000 is 60% by mass or more of the total amount of the low-molecular hyaluronic acid having a molecular weight of 380 to 5000.

[6] The nerve growth promoter according to any one of [1] to [5], wherein the content of N-acetylglucosamine is 0.01% by mass or less relative to the total amount of the nerve growth promoter.

[7] The nerve growth promoter according to any one of [1] to [6], wherein a total free amino acid amount is 2% by mass or more as a ratio by mass to the total amount of the nerve growth promoter, and a total protein amount is 2% by mass or more as a ratio by mass to the total amount of the nerve growth promoter.

[8] The nerve growth promoter according to [7], wherein the free amino acid contains at least one selected from isoleucine, p-aminoisobutyric acid, alanine, taurine, phenylalanine, aspartic acid, cystine and tyrosine.

[9] The nerve growth promoter according to any one of [1] to [8], containing a ground product obtained by grinding a freeze-dried product of the degradation product.

[10] The nerve growth promoter according to any one of [1] to [9], containing a water-saturated 1-butanol fraction obtained through liquid-liquid separation of the degradation product with water and water-saturated 1-butanol.

[11] The nerve growth promoter according to any one of [1] to [10], having an effect of promoting formation of neurites from a nerve system.

[12] The nerve growth promoter according to any one of [1] to [11], having an effect of promoting growth of neurites.

[13] The nerve growth promoter according to any one of [1] to [12], having an effect of promoting differentiation of stem cells into nerve cells.

[14] The nerve growth promoter according to any one of [1] to [13], having an effect of promoting formation and growth of nerve growth factor-induced neurites.

[15] A method for producing a nerve growth promoter, including an enzyme treatment step of degrading a composition containing a hyaluronic acid and a protein with a protease.

[16] The method for producing a nerve growth promoter according to [15], in which the composition is a comb and which includes, prior to the enzyme treatment step, a step of chipping the comb into pieces of 0.5 cm square or more.

[17] The method for producing a nerve growth promoter according to [15] or [16], which includes, after the enzyme treatment step, a step of freeze-drying the degradation product obtained in the enzyme treatment step, and then grinding it into a ground product.

[18] The method for producing a nerve growth promoter according to any one of [15] to [17], which includes, after the enzyme treatment step, a purification step of purifying the degradation product obtained in the enzyme treatment step.

[19] The method for producing a nerve growth promoter according to [18], wherein the purification step includes a liquid-liquid separation step for liquid-liquid separation of the degradation product with water and water-saturated 1-butanol to give a water-saturated 1-butanol fraction.

[20] An internal preparation containing the nerve growth promoter of any one of [1] to [14].

[21] A medium additive containing the nerve growth promoter of any one of [1] to [14].

[22] A cell dilution additive containing the nerve growth promoter of any one of [1] to [14].

[23] A medium containing the medium additive of [21].

[24] A cell dilution containing the cell dilution additive of [22].

[25] An antioxidant containing a degradation product obtained by degrading a composition containing a hyaluronic acid and a protein with a protease.

[26] The antioxidant according to [25], wherein the composition is a comb.

[27] The antioxidant according to [25] or [26], wherein the degradation product contains a low-molecular hyaluronic acid having a molecular weight of 380 to 5000.

[28] The antioxidant according to any one of [25] to [27], wherein the content of the low-molecular hyaluronic acid having a molecular weight of 380 to 5000 is 10% by mass or more relative to the total amount of the antioxidant.

[29] The antioxidant according to [27] or [28], wherein the proportion of a low-molecular hyaluronic acid having a molecular weight of 1520 to 5000 is 60% by mass or more of the total amount of the low-molecular hyaluronic acid having a molecular weight of 380 to 5000.

[30] The antioxidant according to any one of [25] to [29], wherein the content of N-acetylglucosamine is 0.01% by mass or less relative to the total amount of the antioxidant.

[31] The antioxidant according to any one of [25] to [30], wherein a total free amino acid amount is 2% by mass or more as a ratio by mass to the total amount of the antioxidant, and a total protein amount is 2% by mass or more as a ratio by mass to the total amount of the antioxidant.

[32] The antioxidant according to [31], wherein the free amino acid contains at least one selected from isoleucine, pi-aminoisobutyric acid, alanine, taurine, phenylalanine, aspartic acid, cystine and tyrosine.

[33] The antioxidant according to any one of [25] to [32], containing a ground product obtained by grinding a freeze-dried product of the degradation product.

[34] The antioxidant according to any one of [25] to [33], containing a water-saturated 1-butanol fraction obtained through liquid-liquid separation of the degradation product with water and water-saturated 1-butanol.

[35] The antioxidant according to any one of [25] to [34], having an effect of trapping radials.

[36] The antioxidant according to any one of [25] to [35], having an effect of preventing oxygenation failures of biogenic substances.

[37] A method for producing an antioxidant, including an enzyme treatment step of degrading a composition containing a hyaluronic acid and a protein with a protease.

[38] The method for producing an antioxidant according to [37], in which the composition is a comb and which includes, prior to the enzyme treatment step, a step of chipping the comb into pieces of 0.5 cm square or more.

[39] The method for producing an antioxidant according to [37] or [38], which includes, after the enzyme treatment step, a step of freeze-drying the degradation product obtained in the enzyme treatment step, and then grinding it into a ground product.

[40] The method for producing an antioxidant according to any one of [37] to [39], which includes, after the enzyme treatment step, a purification step of purifying the degradation product obtained in the enzyme treatment step.

[41] The method for producing an antioxidant according to [40], wherein the purification step includes a liquid-liquid separation step for liquid-liquid separation of the degradation product with water and water-saturated 1-butanol to give a water-saturated 1-butanol fraction.

[42] An internal preparation containing the antioxidant of any one of [25] to [36].

[43] An external preparation containing the antioxidant of any one of [25] to [36].

[44] The external preparation according to [43], which is a cosmetic product.

[45] A wound treatment agent containing an ethyl acetate extract of a degradation product obtained by degrading a composition containing a hyaluronic acid and a protein with a protease.

[46] The wound treatment agent according to [45], wherein the composition is a comb.

[47] The wound treatment agent according to [45] or [46], wherein the degradation product contains a low-molecular hyaluronic acid having a molecular weight of 380 to 5000.

[48] The wound treatment agent according to any one of [45] to [47], wherein the content of the low-molecular hyaluronic acid having a molecular weight of 380 to 5000 is 10% by mass or more relative to the total amount of the wound treatment agent.

[49] The wound treatment agent according to [47] or [48], wherein the proportion of a low-molecular hyaluronic acid having a molecular weight of 1520 to 5000 is 60% by mass or more of the total amount of the low-molecular hyaluronic acid having a molecular weight of 380 to 5000.
- [50] The wound treatment agent according to any one of [45] to [49], wherein the content of N-acetylglucosamine is 0.01% by mass or less relative to the total amount of the wound treatment agent.
- [51] The wound treatment agent according to any one of [45] to [50], wherein a total free amino acid amount is 2% by mass or more as a ratio by mass to the total amount of the wound treatment agent, and a total protein amount is 2% by mass or more as a ratio by mass to the total amount of the wound treatment agent.
- [52] The wound treatment agent according to [51], wherein the free amino acid contains at least one selected from isoleucine, p-aminoisobutyric acid, alanine, taurine, phenylalanine, aspartic acid, cystine and tyrosine.
- [53] The wound treatment agent according to any one of [45] to [52], containing an ethyl acetate extraction of a ground product obtained by grinding a freeze-dried product of the degradation product.
- [54] The wound treatment agent according to any one of [45] to [53], wherein the ethyl acetate extract is an ethyl acetate fraction obtained through liquid-liquid separation of the degradation product with ethyl acetate and water.
- [55] The wound treatment agent according to any one of [45] to [54], having an effect of promoting migration of fibroblasts.
- [56] A method for producing a wound treatment agent, including an enzyme treatment step of obtaining a degradation product by degrading a composition containing a hyaluronic acid and a protein with a protease, and a liquid-liquid separation step for liquid-liquid separation of the degradation product with ethyl acetate and water to give an ethyl acetate fraction.
- [57] The method for producing a wound treatment agent according to [56], in which the composition is a comb and which includes, prior to the enzyme treatment step, a step of chipping the comb into pieces of 0.5 cm square or more.
- [58] The method for producing a wound treatment agent according to [56] or [57], which includes, after the enzyme treatment step, a step of freeze-drying the degradation product obtained in the enzyme treatment step, and then grinding it into a ground product and wherein:
  the ethyl acetate fraction is obtained through liquid-liquid separation of the ground product with ethyl acetate and water in the liquid-liquid separation step.
- [59] The method for producing a wound treatment agent according to any one of [56] to [58], which includes, after the liquid-liquid separation step, a purification step of purifying the ethyl acetate fraction obtained in the liquid-liquid separation step.
- [60] An internal preparation containing the wound treatment agent of any one of [45] to [55].
- [61] An internal preparation containing the wound treatment agent of any one of [45] to [55].
- [62] The external preparation according to [61], which is a cosmetic product.

Advantageous Effects of Invention

The nerve growth promoter of the present invention has an effect of effectively promoting formation and growth of neurites in nerve cells and provides a high nerve growth promoting effect. The antioxidant of the present invention has a high antioxidant effect and can effectively prevent oxygenation failures of biogenic substances. The wound treatment agent of the present invention exhibits a high wound healing promoting effect at a relatively low concentration, and when administered to a wounded living organism, the agent can rapidly heal the wound. According to the production methods of the present invention, the nerve growth promoter, the antioxidant and the wound treatment agent having the above-mentioned useful effects can be produced at low cost.

BRIEF DESCRIPTION OF DRAWINGS

FIG. 1 This is a graph showing a neurite formation rate in a medium of PC-12 cells added with or not added with dibutyryl cAMP, to which a freeze-dried powder of a protease-degraded product (nerve growth promoter 1) was added at different concentrations.

FIG. 2 This is a graph showing a neurite formation rate in a medium of PC-12 cells added with NGF, to which a freeze-dried powder of a protease-degraded product (nerve growth promoter 1) was added at different concentrations.

FIG. 3 This is a graph showing a neurite formation rate in a medium of PC-12 cells added with dibutyryl cAMP, to which a freeze-dried powder of a protease degraded product (nerve growth promoter 1), or a water-saturated 1-butanol (1-BuOH) fraction, an ethyl acetate (EtOAc) fraction or a water fraction thereof was added at different concentrations.

FIG. 4 This is a scheme drawing that shows a purification step for a protease-degraded product in Example 1.

FIG. 5 This is a graph showing a trapping activity of a protease-degraded product (antioxidant 1), ascorbic acid and arbutin for ABTS radical cations.

FIG. 6 This is a graph showing an antioxidant activity of a protease-degraded product (antioxidant 1) and ascorbic acid against alkoxy radicals and peroxy radicals, as measured according to an ORAC method.

FIG. 7 This is a graph showing results of an oxystress-induced erythrocyte hemolysis inhibition test with a protease-degraded product (antioxidant 1) and ascorbic acid.

FIG. 8 This is a graph showing a trapping activity of a water-saturated 1-butanol fraction, a water fraction and an ethyl acetate fraction obtained in liquid-liquid separation of a protease-degraded product, for ABTS radical cations.

FIG. 9 This is a scheme drawing that shows a purification step for a protease-degraded product in Example 2.

FIG. 10 This is a drawing for explaining an evaluation method for a wound healing promoting effect, in which (a) is a schematic view showing a way of scratching a cell group in a well, and (b) is a schematic view showing the longest migration distance between the scratch and the cells.

FIG. 11 This is a graph showing a cell migration distance measured in evaluation of the wound healing promoting effect of an ethyl acetate fraction of a protease-degraded product (wound treatment agent 1), a freeze-dried powder of a protease-degraded product, and a water fraction and a water-saturated 1-butanol fraction of a protease-degraded product.

FIG. 12 This is a scheme drawing that shows a purification step for a protease-degraded product in Example 3.

DESCRIPTION OF EMBODIMENTS

The present invention is described in detail hereinunder. The description of the constitutive elements of the invention given hereinunder is for some typical embodiments or examples of the invention, to which, however, the invention should not be limited. In this description, the numerical range expressed by the wording "a number to another number" means the range that falls between the former number indicating the lower limit of the range and the latter number indicating the upper limit thereof.

1. Nerve Growth Promoter

[Details of Nerve Growth Promoter]

The nerve growth promoter of the present invention is characterized by containing a degradation product obtained by degrading a composition containing a hyaluronic acid and a protein with a protease.

With no specific limitation, the hyaluronic acid contained in the composition may be any hyaluronic acid that is generally used as a component for cosmetics and medicines. Originally, a hyaluronic acid is isolated from a bovine vitreous body, but not limited thereto, any one isolated from an animal joint fluid or a cock's comb is usable here. Not one isolated from the natural field but any other obtained by synthesis or according to microbial fermentation may also be usable.

Hyaluronic acid is a complicated polysaccharide of amino acids and uronic acids, and the details of the structure are not specifically limited. For example, there can be mentioned a polysaccharide having a recurring unit of dioses of D-glucuronic acid and N-acetyl-D-glucosamine. The molecular weight of the hyaluronic acid contained in the composition is not specifically limited, and for example, the hyaluronic acid extracted from a cock's comb has a molecular weight of 6,000,000 to 10,000,000, but the hyaluronic acid extracted from a cock's comb has a mean molecular weight of hundreds of thousands to millions as it is degraded in the extraction process. The hyaluronic acid for use in the present invention may be an induced one or a thermally-denatured one so far as it does not too excessively lose a nerve growth promoting effect. Compound known as so-called hyaluronic acid derivatives can be effectively used in the present invention.

The protein contained in the composition may be any one irrespective of the kind thereof, but is extremely preferably a protein contained in a comb. The kind of the comb is not specifically limited, but using a cock's comb is preferred. A cock's comb contains a hyaluronic acid and is therefore advantageous in that any additional hyaluronic acid does not need to be separately added thereto in providing the composition for use for producing the nerve growth promoter of the present invention. Consequently, when a cock's comb is used, the production process for the nerve growth promoter of the present invention can be simplified and the production cost can be thereby reduced.

The composition for use in the present invention may contain only a protein and a hyaluronic acid, but may contain any other component, solvent or dispersion medium. The solvent and the dispersion medium may be any one capable of dissolving a protein and a hyaluronic acid, and water and an aqueous buffer are favorably used. The composition may be a natural substance itself containing a protein and a hyaluronic acid. The natural substance to be the composition includes an animal joint fluid and a comb, and a cock's comb is especially preferred as rich in a hyaluronic acid.

The degradation product for use in the present invention is one obtained by degrading the above-mentioned composition with a protease. The kind of the protease is not specifically limited. Any protease usable for ordinary proteolysis is usable here. Specifically, an endopeptidase or an exopeptidase is usable, and the active site may be any of serine, cystine, metal, aspartic acid, etc. Plural proteases may be mixed and used here. As a preferred protease, for example, a pronase may be used.

The degradation product for use in the present invention is one obtained by degrading the above-mentioned composition with a protease, and therefore contains at least a protein-degraded product that has been degraded with a protease, and a hyaluronic acid, and may contain an undegraded protein (a protein naturally contained in the composition before protease addition thereto) and any other component derived from the composition.

The protein-degraded product contained in the degradation product includes a protein, a peptide and a free amino acid having a lower molecular weight than that of the undegraded protein, and these may exist in the degradation product as mixed therein.

Preferably, the degradation product contains a free amino acid. The free amino acid that the degradation product contains may be a free amino acid as a protein-degraded product, or a free amino acid naturally contained in the composition before protease addition thereto. The kind of the free amino acid varies depending on the components of the composition. For example, in the degradation product from a composition of a comb, amino acids such as isoleucine, p-aminoisobutyric acid, alanine, taurine, phenylalanine, aspartic acid, cystine and tyrosine are contained in a relatively high content, and in addition to these, other various kinds of amino acids are contained therein.

The total protein amount in the nerve growth promoter is preferably 0.5 to 10% by mass as a ratio by mass to the total amount of the nerve growth promoter, more preferably 1 to 7% by mass, even more preferably 2 to 5% by mass. The total free amino acid amount in the nerve growth promoter is preferably 0.5 to 12% by mass as a ratio by mass to the total amount of the nerve growth promoter, more preferably 1 to 8% by mass, even more preferably 2 to 6% by mass. When the total protein amount and the free amino acid amount in the nerve growth promoter each fall within the above-mentioned range, the nerve growth promoter is considered to effectively act so as to noticeably promote formation and growth of neurites in nerve cells.

In this description, the "total protein amount" means a total protein content determined according to a Lowry method; and the "total free amino acid amount" is a total amount of free amino acids determined according to a ninhydrin method.

The hyaluronic acid contained in the degradation product may be the hyaluronic acid that has been naturally contained in the composition before protease addition and has remained therein as such (hereinafter referred to as "undegraded hyaluronic acid"), or a degradation product of a hyaluronic acid (hereinafter referred to as "low-molecular hyaluronic acid"), or a mixture of the undegraded hyaluronic acid and the low-molecular hyaluronic acid, and preferably, the degradation product contains a low-molecular hyaluronic acid. A low-molecular hyaluronic acid can readily penetrate into the depth of a living organism and can effectively act on a living organism. The low-molecular hyaluronic acid that the degradation product contains may be a low-molecular hyaluronic acid obtained by hydrolyzing the hyaluronic acid in the composition, or a low-molecular hyaluronic acid prepared by hydrolyzing a hyaluronic acid in a system different from the composition may be added to the degradation product. Preferably, a low-molecular hyaluronic acid obtained by hydrolyzing the hyaluronic acid in the composition is contained in the degradation product.

For producing a low-molecular hyaluronic acid in the composition, a substance capable of hydrolyzing a hyaluronic acid, such as hydrochloric acid or hyaluronidase may be added to the composition in which the hyaluronic acid is to be hydrolyzed. In the case where the composition is a natural substance, a low-molecular hyaluronic acid may be produced through autolysis with a substance originally contained in the natural substance. However, from the viewpoint of effectively realizing the action of a hyaluronic acid on a living organism, preferably, the hyaluronic acid maintains the structural unit thereof, that is, the hyaluronic acid is not degraded to glucuronic acid and N-acetyl glucosamine. Specifically, the N-acetylglucosamine content in the nerve growth promoter is preferably 0.01% by mass or less relative to the total amount of the nerve growth promoter, and is most preferably 0% by mass.

In this description, the "N-acetylglucosamine amount" is an N-acetylglucosamine content determined according to a Morgan-Elson method.

The molecular weight of the low-molecular hyaluronic acid that the degradation product contains is preferably 380 to 5000. The molecular weight of 380 to 5000 corresponds to about 1 to 14 recurring units of hyaluronic acid. The content of the low-molecular hyaluronic acid having a molecular weight of 380 to 5000 in the nerve growth promoter is preferably 5% by mass or more relative to the total amount of the nerve growth promoter, more preferably 7% by mass or more, even more preferably 10% by mass or more. Preferably, the main component of the low-molecular hyaluronic acid is a low-molecular hyaluronic acid having a molecular weight of 1520 to 5000, more preferably the proportion of a low-molecular hyaluronic acid having a molecular weight of 1520 to 5000 is 60% by mass or more of the total amount of the low-molecular hyaluronic acid having a molecular weight of 380 to 5000, even more preferably 70% by mass or more, and further more preferably 75% by mass or more. With that, it is considered that the nerve growth promoter can effectively act to noticeably promote formation and growth of neurites in nerve cells.

The molecular weight and the mass ratio of the low-molecular hyaluronic acid can be determined through analysis of high-performance liquid chromatography using polyethylene glycol as a molecular weight marker.

The properties of the degradation product vary depending on the components and the composition ratio of the composition and the kind of the protease to be used. In general, the degradation product is liquid, precisely viscous liquid. The degradation product may be used as the nerve growth promoter of the present invention directly as it is, but may be suitably purified and combined with any other component to be the nerve growth promoter of the present invention. By purifying the degradation product, a nerve growth promoter having a higher nerve growth promoting effect can be provided. A liquid nerve growth promoter can be used as an external preparation for external application or ocular instillation, or as an internal preparation of a type of drink. In the case where a degradation product is dried by freeze drying or the like and then ground, a powdery nerve growth promoter can be provided. The powdery nerve growth promoter can be used as an internal preparation directly as it is, or after mixed with any other component, or may be processed into tablets or capsules, or a desired solvent or dispersion medium may be added thereto to form a liquid, and the resultant liquid may be used as an external preparation for external application or ocular instillation, or as an internal preparation of a type of drink.

The nerve growth promoter of the present invention may contain any other various components than the above-mentioned degradation product. For example, in the case where a vehicle is added to the nerve growth promoter, the blend ratio of the degradation product and the vehicle may be controlled to thereby control the component amount such as the total protein amount, the total free amino acid amount and the low-molecular hyaluronic acid amount. An embodiment of the nerve growth promoter that is easy to store is a mixture powder produced by diluting a ground powder of a freeze-dried degradation product with a vehicle. The vehicle is not specifically limited, but is preferably dextrin. The dilution ratio with the vehicle is preferably 2 to 10 times as a ratio by mass, more preferably 2 to 7 times, even more preferably 3 to 5 times.

The nerve growth promoter of the present invention has an effect of promoting formation and growth of neurites in nerve cells (nerve growth promoting effect), and in particular, can effectively promote formation and growth of neurites induced by a nerve growth factor (NGF).

Accordingly, in the case where the nerve growth promoter of the present invention is taken orally and where the components thereof are absorbed by the intestinal tract, the promoter effectively promotes formation and growth of neurites in the nerve system where it has reached to thereby contribute toward reconstruction of the nerve circuit damaged by denaturation or damage of neurites. Accordingly, the nerve growth promoter can effectively relieve the disorders of cognitive function and motor function caused by nerve denaturation trouble or nerve damage. Here, the nerve growth promoter of the present invention is highly safe as using a hyaluronic acid and a protein that are biogenic substances and an enzyme that reacts mildly, and therefore has an advantage in that the nerve growth promoter can be used as an internal preparation to be taken orally with ease.

The nerve growth promoter of the present invention has an effect of promoting differentiation of stem cells cultivated in a medium, into nerve cells. Accordingly, the nerve growth promoter of the present invention can be effectively used as a differentiation promoter of promoting differentiation of stem cells into nerve cells, in the regenerative medicine area utilizing pluripotent stem cells such as iPS cells or neural precursors. With that, production of nerve cells from stem cells can be attained efficiently, and the nerve growth promoter of the present invention can greatly contribute toward production efficiency increase and cost reduction in regenerative medicine-related various industries.

The amount of the nerve growth promoter of the present invention to be used varies depending on the targeted failure and is, for example, the following dose is preferred.

For example, in the case where the nerve growth promoter of the present invention is orally administered as an internal preparation, the dose thereof is preferably 80 to 2000 mg/adult standard body weight/day, and multiple dosage of two or three times a day is suitable.

In the case where the nerve growth promoter of the present invention is added to a medium for cultivating pluripotent stem cells or neural precursors, the amount thereof to be added is preferably 0.1% by mass or more as a ratio by mass to the total amount, more preferably 0.2% by mass or more, and even more preferably 0.2 to 1.0% by mass. The amount to be added as a protease-degraded product is preferably 0.03% by mass or more in terms of the freeze-dried product thereof, more preferably 0.05% by mass or more, and even more preferably 0.05 to 0.25% by mass.

[Method for Producing Nerve Growth Promoter]

Next, a method for producing the nerve growth promoter of the present invention is described.

A method for producing the nerve growth promoter of the present invention is characterized by including an enzyme treatment step of degrading a composition containing a hyaluronic acid and a protein with a protease.

The production method for the nerve growth promoter of the present invention may have, further if desired, any other step. For example, in the case where the composition is a comb, the production method may have a chipping step of chipping a comb, prior to the enzyme treatment step. In addition, the production method may have, after the enzyme treatment step, a filtration step of filtrating the degradation product, a powdering step of drying and grinding the filtrated degradation product, and a purification step of purifying the filtered degradation product. In the following, the production method for the nerve growth promoter of the present invention is described in detail.

First, a composition containing a hyaluronic acid and a protein is prepared. In the case where a cock's comb is used as the composition, any one is usable irrespective of age and sex. Preferably, however, a cock's comb is processed for protease degradation shortly after its collection. In the case where a cock's comb is processed for protease degradation long after its collection, preferably, it is once freeze-dried and then thawed before use.

In protease degradation of a comb, preferably, the comb is processed in a chipping step of chipping it, and then the resultant comb pieces are brought into contact with a protease-containing solution. The comb is preferably chipped into pieces of 0.5 cm square or more, more preferably 0.7 cm square or more, even more preferably 0.9 cm square or more. If too much chipped or minced, water may excessively flow out of the resultant pieces, unfavorably.

Next, the composition is processed in an enzyme treatment step of degrading it with a protease. Regarding the protease for use in the production method of the present invention, the description of protease in the column of [Nerve Growth Promoter] given hereinabove may be referred to. Enzyme treatment varies depending on the kind of the composition and the protease. For example, in the case where the composition is a solid or a powder of a comb or the like, preferably, a solution such as an aqueous solution where a protease has been dissolved therein (enzyme solution) is added thereto and the left as such for a predetermined period of time. Here, the pH of the enzyme solution is preferably 5.0 to 10.0, the treatment temperature is preferably 40 to 60° C., and the treatment time is preferably 0.5 to 3.0 hours. Also preferably, the enzyme treatment is carried out while the composition to which the enzyme solution has been added is shaken.

From the degradation product obtained in the manner as above, a solid fraction of comb and others may be removed through filtration or the like, and the resultant liquid may be used as a liquid degradation product. If desired, the product may be further processed in a powdering step of drying it by freeze-drying or the like followed by further grinding it to give a powdery degradation product for use herein. The degradation product may be used as the nerve growth promoter of the present invention directly as it is, or may be used as the nerve growth promoter after optionally purified or combined with any other component such as a vehicle.

The nerve growth promoter of the present invention may be produced according to such an extremely simple process. Therefore, using the production method for the nerve growth promoter of the present invention, a high-useful nerve growth promoter can be provided at low cost.

In addition, by purifying the filtered degradation product or the powdery degradation product, a nerve growth promoter having a higher nerve growth promoting effect can be provided. For the details of the purification method for the degradation product, the column of <Purification of Protease Degradation Product> in Example 1 to be given below is referred to. In purifying the degradation product, preferably, the degradation product is processed for liquid-liquid separation with water and water-saturated 1-butanol. The water-saturated 1-butanol fraction obtained through the liquid-liquid separation contains a component having a high nerve growth promoting effect, and by further purification treatment of column chromatography or the like, a nerve growth promoter having an extremely high nerve growth promoting effect can be obtained.

[Use of Nerve Growth Promoter]

As described above, the nerve growth promoter of the present invention has a nerve growth promoting effect and has an effect of promoting differentiation of stem cells such as pluripotent stem cells or neural precursors into nerve cells.

Consequently, the nerve growth promoter of the present invention can be effectively used as an internal preparation which is administered to animals such as human beings to relieve functional disorders thereof caused by neurodegenerative disorders or nerve damages. The nerve growth promoter as an internal preparation may optionally contain any other various components than the above-mentioned degradation product and vehicle. For example, vitamins, vegetable powders, minerals, yeast extracts, colorants and tackifiers may be optionally added thereto. The kind of these components is not specifically limited, and the content thereof may be appropriately controlled within a range capable of sufficiently exhibiting the intended function.

In the regenerative medicine area utilizing pluripotent stem cells such as iPS cells or neural precursors, the nerve growth promoter of the present invention may be added to a diluent for a medium or cells and can be favorably used as a differentiation promoter of promoting differentiation of such stem cells into nerve cells. The medium to which the nerve growth promoter is added may be any of liquid (bouillon) media, semi-fluid media, or solid (agar) media, and the composition thereof is not specifically limited. The diluent may be any one ordinary used in the art as a diluent for cells, such as a physiological saline solution, and the nerve growth promoter of the present invention is applicable to any of them.

2. Antioxidant

[Details of Antioxidant]

For the raw materials, the components, the composition, the production, the application aspect of the antioxidant of the present invention and preferred embodiments thereof, the description relating to the raw materials, the components, the composition, the production, and the application aspect of the nerve growth promoter mentioned above and the preferred embodiments thereof may be referred to.

The antioxidant of the present invention has an effect of trapping radicals and exhibits a high antioxidation activity.

Here, in this description, "antioxidation activity" means a property of preventing oxidation, and includes a function of preventing oxygenation failures of biogenic substances (DNA, lipid, enzyme, protein, etc.), and in addition thereto, also includes a function of preventing deterioration by oxidation of foods and others. The antioxidant of the present invention exhibits both the two functions, but owing to especially high usefulness thereof, the function of preventing oxygenation failures of biogenic substances is preferably utilized.

The radicals to be trapped by the antioxidant of the present invention are not specifically limited, and they may be radicals as active oxygen or may also be any other radicals than active oxygen. Specific examples of the radicals include super oxide ($\cdot O_2^-$), hydroxyl radical (HO·), hydroperoxyl radical (HOO·), alkoxyl radical (RO·), and alkylperoxyl radical (ROO·).

As in the above, the antioxidant of the present invention has a high antioxidation activity, and therefore when it is taken orally and when the components thereof are absorbed by the intestinal tract, the antioxidant can trap active oxygen generated in the living organism and can effectively inhibit oxygenation failures of the biogenic substances. As a result, progression of aging can be retarded and development of lifestyle-related diseases and other various oxystress-induced diseases such as cancers can be prevented.

Here, the antioxidant of the present invention is highly safe as using a hyaluronic acid and a protein that are biogenic substances and an enzyme that reacts mildly, and therefore has an advantage in that the antioxidant can be used as an internal preparation to be taken orally with ease.

In addition, the antioxidant of the present invention is applicable to the skin. The components absorbed inside through the skin trap the active oxygen generated in the epidermis, the dermis and the hypodermis to thereby effectively prevent various disorders such as skin aging and inflammation and pigmentation. The components not having been absorbed through the skin into the living body but having remained on the skin surface trap the active oxygen generated in the skin surface or around the skin surface to thereby effectively prevent various disorders such as skin aging and inflammation and pigmentation owing to active oxygen. The antioxidant of the present invention undergoes protease degradation, and therefore by changing the condition thereof, absorption from the skin may be controlled and accordingly, the antioxidant may be made to predominantly act on specific sites (for example, on the skin surface, around the skin surface or the depth of the skin).

The amount of the antioxidant of the present invention to be used varies depending on the targeted failure and is, for example, in the case where the antioxidant of the present invention is orally administered as an internal preparation, the dose thereof is preferably 80 to 2000 mg/adult standard body weight/day, and multiple dosage of two or three times a day is suitable.

In the case where the antioxidant of the present invention is applied to the skin as a cosmetic or an external preparation, the coating amount thereof is preferably 0.5 g to 5.0 g/10 cm$^2$, and the use frequency is suitably 1 to 4 times/day or so.

[Use of Antioxidant]

As described above, the antioxidant of the present invention has a high antioxidation activity and can effectively prevent oxygenation failures of biogenic substances. Consequently, the antioxidant of the present invention can be effectively used as an internal preparation and an external preparation to be administered to animals such as human beings. In the case were the antioxidant of the present invention is an external preparation, it may be an external medication or a cosmetic product. In the case of a cosmetic product, for example, the antioxidant is favorably used in embodiments of basic skin care products such as milk, cream, lotion and essence, and makeup cosmetic products such as lipstick, foundation, liquid foundation, makeup pressed powder, face powder, and eyeshadow.

The antioxidant of the present invention may contain any other various components than the above-mentioned degradation product and vehicle, depending on the use thereof. For example, vitamins, vegetable powders, minerals, yeast extracts, colorants and tackifiers may be optionally added thereto. The kind of these components is not specifically limited, and the content thereof may be appropriately controlled within a range capable of sufficiently exhibiting the intended function.

In a cosmetic product of the antioxidant, compounding components that are generally used in cosmetics, for example, an oily component, a surfactant, a moisturizer, a tackifier, an antiseptic/microbial agent, a powder component, a UV absorbent, a colorant, and a fragrance may be optionally incorporated.

3. Wound Treatment Agent

[Details of Wound Treatment Agent]

The wound treatment agent of the present invention is characterized by containing an ethyl acetate extract of a degradation product prepared by degrading a composition containing a hyaluronic acid and a protein with a protease.

For the raw materials, the components, the composition, the production, the application aspect of the antioxidant of the "degradation product prepared by degrading a composition containing a hyaluronic acid and a protein with a protease" before ethyl acetate extraction, and preferred embodiments thereof, the description relating to the raw materials, the components, the composition and the production of the nerve growth promoter mentioned above and the preferred embodiments thereof may be referred to.

The extraction method using ethyl acetate is not specifically limited, and the method may be a liquid-liquid separation method (liquid-liquid extraction method) using a solvent immiscible with ethyl acetate, or a solvent extraction method (solid-liquid extraction method) using ethyl acetate as an extraction solvent, but since the degradation product is generally liquid, a liquid-liquid separation method is popular. Here, the "immiscible solvent" in the liquid-liquid separation method means a solvent that does not mix with ethyl acetate when brought into contact with it, and separates from each other. Specifically, the solvent of the type includes water, hexane, chloroform, and ether, and water is preferred. The ethyl acetate extract obtained in the liquid-liquid separation method or the solvent extraction method is liquid, and may be used as the wound treatment agent of the present invention directly as it is, of may be suitably combined with any other component to be the wound treatment agent of the present invention. By purifying the ethyl acetate extract, a wound treatment agent having a higher wound healing promoting effect can be obtained. The liquid wound treatment agent can be used as an external preparation for external application or ocular instillation, or as an internal preparation of a type of drink. In the case where the ethyl acetate extract is dried by freeze-drying and the ground, a powdery wound treatment agent can be provided. The powdery wound treatment agent may be used for an external preparation directly as it is, or after mixed with any other component, the agent may be processed into tablets or capsules, or a desired solvent or a dispersion medium may be added thereto to give a liquid agent, and the resultant liquid agent may be used as an external preparation for external application or ocular instillation, or as an internal preparation of a type of drink.

The wound treatment agent of the present invention may contain any other various components than the above-mentioned degradation product. For example, in the case where a vehicle is added to the wound treatment agent, the blend ratio of the ethyl acetate extract and the vehicle may be controlled to thereby control the component amount such as the total protein amount, the total free amino acid amount and the low-molecular hyaluronic acid amount. An embodiment of the wound treatment agent that is easy to store is a mixture powder produced by diluting a ground powder of a freeze-dried ethyl acetate extract with a vehicle. The vehicle is not specifically limited, but is preferably dextrin. The dilution ratio with the vehicle is preferably 2 to 10 times as a ratio by mass, more preferably 2 to 7 times, even more preferably 3 to 5 times.

When the wound treatment agent is administered, migration of fibroblasts to the wounded site is noticeably activated (promoted) to enhance would healing. Accordingly, wound can be rapidly healed. Another advantage of the wound treatment agent of the present invention is that a region wounded after preliminary administration of the wound treatment agent can be rapidly healed. Here, the wound treatment agent of the present invention contains an ethyl acetate extract of a degradation product obtained by degrading a composition containing a hyaluronic acid and a protein with a protease, but not the degradation product itself, and therefore, the wound treatment agent of the present invention can exhibit a high wound healing promoting effect even at an markedly lower concentration than the concentration of a wound treatment agent containing the degradation product itself. Consequently, even when any other component and a vehicle are added thereto, the wound treatment agent of the present invention can exhibit a sufficient wound healing promoting effect, and has an advantage in that the preparation containing the agent can be readily improved. In addition, the amount of the raw materials to be used per the unit preparation can be greatly suppressed, and the production cost can be thereby significantly reduced.

The administration route of the wound treatment agent of the present invention is not specifically limited, and the agent may be administered orally or may be directly applied to a region of wound. In the case where the wound treatment agent of the present invention is taken orally, the components of the wound treatment agent absorbed by the intestinal tract can exhibit a healing promoting effect not only on surface wounds but also on wounds in the body, and therefore can rapidly heal these wounds. The oral administration is effective for the cases having many wounds throughout the whole body, for the cases having a wound in a region local medication by the patient itself is difficult, and for the cases of wounded infants or wounded senior adults who could hardly realize their wounds. Here, the wound treatment agent of the present invention is highly safe as using a hyaluronic acid and a protein that are biogenic substances and an enzyme that reacts mildly, and therefore has an advantage in that the wound treatment agent can be used as an internal preparation to be taken orally with ease.

In addition, the wound treatment agent of the present invention is applicable to the skin. In the case where the wound treatment agent of the present invention is applied to the skin, the components of the wound treatment agent having been absorbed through the skin may locally act on the wound around the applied region and can rapidly heal the wound.

The wound healing effect in the present invention can be enhanced for the first time by combining a hyaluronic acid and a degradation product of a protein and further by administering a component extracted from them with ethyl acetate (ethyl acetate extract). Such a wound treatment effect can be further enhanced by additionally administering vitamins such as ascorbic acid and vegetable powders simultaneously with the ethyl acetate extract. Vegetable powders are those prepared by powdering vegetables typified by carrots, and an extract alone thereof may be used. The solid weight ratio of the vegetable powder relative to the ester extract is preferably within a range of 1/100 to 100/1, more preferably within a range of 1/10 to 10/1, and even more preferably within a range of 1/2 to 2/1.

The dose of the wound treatment agent of the present invention may be appropriately determined taking the age, the body weight, the wound condition, the wound position and the administration route of the targeted case into consideration. For example, in the case where the wound treatment agent of the present invention is orally administered as an internal preparation, the dose thereof is preferably 80 to 2000 mg/adult standard body weight/day, and multiple dosage of two or three times a day is suitable.

In the case where the wound treatment agent of the present invention is applied to the skin as a cosmetic or an external preparation, the coating amount thereof is preferably 0.5 g to 5.0 g/10 cm$^2$, and the use frequency is suitably 1 to 4 times/day or so.

[Method for Producing Wound Treatment Agent]

A method for producing the wound treatment agent of the present invention is characterized by including an enzyme treatment step of degrading a composition containing a hyaluronic acid and a protein with a protease to give a degradation product, and a liquid-liquid separation step for liquid-liquid separation of the degradation product with ethyl acetate and water to give an ethyl acetate fraction. In this, for the enzyme treatment step of giving a degradation product, the description relating to the production process for a nerve growth promoter and the preferred embodiment thereof given hereinabove are referred to.

The ratio by volume of ethyl acetate to water for use in the liquid-liquid separation step is preferably 1/1 to 10/1, more preferably 1/1 to 5/1, even more preferably 1/1 to 3/1. The environment temperature in the liquid-liquid separation is preferably 0 to 70° C., more preferably 10 to 50° C., even more preferably 20 to 30° C. The liquid-liquid separation may be carried out once alone, or may be carried our plural times. Preferably, the operation is carried out plural times. The order of the liquid-liquid separation is not specifically limited, and the operation may be carried out according to an ordinary liquid-liquid separation sequence. As one preferred method, there may be mentioned a method of putting a diluted liquid prepared by diluting a freeze-dried product of a degradation product with water into a separating funnel, adding ethyl acetate thereto, and shaking the separating funnel. According to this method, an aqueous fraction is separated in a lower layer and an ethyl acetate fraction is in an upper layer, and the ethyl acetate fraction of the upper layer is collected. In the case where the liquid-liquid separation is carried out plural times, fresh ethyl acetate is added to the aqueous fraction having remained in the separating funnel, then the separating funnel is shaken and the ethyl acetate fraction is collected. The process of liquid-liquid separation is repeated. As a result, the ethyl acetate-soluble components having remained in the aqueous fraction can be more surely extracted. The ethyl acetate fraction obtained in the manner as above can be used as a liquid ethyl acetate extract. This may be dried by freeze-drying and ground, and the resultant powdery ethyl acetate extract may be used here. The ethyl acetate extract may be used as the wound treatment agent of the present invention directly as it is, or may be appropriately purified and combined with any other component such as a vehicle to be the wound treatment agent of the present invention.

The wound treatment agent of the present invention can be produced according to such an extremely simple process. Accordingly, using the production method for the wound treatment agent of the present invention, a high-useful wound treatment agent can be provided at low cost.

In addition, by purifying the ethyl acetate extract, a wound treatment agent having a higher wound healing promoting effect can be provided. For purification of the ethyl acetate extract, column chromatography or the like may be used. For the tails of the purification method, the column of <Purification of Protease Degradation Product" in Example 3 given hereinunder may be referred to.

[Use of Wound Treatment Agent]

As described above, the wound treatment agent of the present invention has a high wound healing promoting effect, and can rapidly heal wounds. Consequently, the wound treatment agent of the present invention can be effectively used as an internal preparation or an external preparation to be administered to animals such as human beings. In the case where the wound treatment agent of the present invention is an external application, it may be an external medication or a cosmetic product. In the case of a cosmetic product, for example, the wound treatment agent is favorably used in embodiments of basic skin care products such as milk, cream, lotion and essence, and makeup cosmetic products such as lipstick, foundation, liquid foundation, makeup pressed powder, face powder, and eyeshadow.

The wound treatment agent of the present invention may contain any other various components than the above-mentioned degradation product and vehicle, depending on the use thereof. For example, vitamins, vegetable powders, minerals, yeast extracts, colorants and tackifiers may be optionally added thereto. The kind of these components is not specifically limited, and the content thereof may be appropriately controlled within a range capable of sufficiently exhibiting the intended function.

In a cosmetic product of the wound treatment agent, compounding components that are generally used in cosmetics, for example, an oily component, a surfactant, a moisturizer, a tackifier, an antiseptic/microbial agent, a powder component, a UV absorbent, a colorant, and a fragrance may be optionally incorporated.

EXAMPLES

The present invention is described more specifically with reference to Examples given below. The materials, the ratio thereof and the operations in the following Examples may be appropriately varied not overstepping the scope and the spirit of the present invention. Accordingly, the range of the present invention should not be interpreted limitatively by the specific examples shown below.

Example 1: Nerve Growth Promoter

Production Example

One kg of freshly collected cock's combs were cut into small pieces of about 1 cm square, and thermally sterilized by steaming at 100° C. Food-derived enzymes mainly containing a protease were added to the small pieces and reacted at 45° C. for 1.5 hours, and then stirred and homogenized. Subsequently, rough solid fragments were removed by filtration to give a liquid degradation product (hereinafter referred to as "protease degradation product"). The protease degradation product had a pH of 6.5, a Brix value of 6.20 and a solid concentration of 5.91% by weight. The protease degradation product was freeze-dried and ground to be a freeze-dried powder of protease degradation product (nerve growth promoter 1). Dextrin in an amount of 3 equivalent times (as a ratio by mass) was added to the freeze-dried powder of protease degradation product to give a dextrin-added freeze-dried powder (nerve growth promoter 1').

[Analysis Methods]

Component analysis of the nerve growth promoters produced in this Example was carried out according to the following methods.

(1) Measurement of Water Content

One g of the nerve growth promoter was heated and dried at 105° C. for 3 hours, and the constant weight thereof was measured with a precision balance to quantify the water content thereof.

(2) Total Nitrogen Determination

The total nitrogen was quantitatively determined according to a semimicro-Kjeldahl method based on an AOAC method.

(3) Free Amino Acid Determination and Amino Acid Composition Analysis

The total free amino acid amount was quantified according to a ninhydrin method. For quantification, a calibration curve of leucine as a standard amino acid was formed and used. The composition of the free amino acid was analyzed using an amino acid automatic analyzer (manufactured by Hitachi Limited, L-8500 Model) equipped with a column for bioanalysis. In the analysis, 50 mg of the nerve growth promoter was dissolved in distilled water, dried into solid under reduced pressure using a rotary evaporator (60° C.), then eluted with 5 mL of 0.02 N hydrochloric acid, and filtered through filter paper and then through a germ-free filter, and 50 μL of the resultant filtrate was used as an analysis sample.

(4) Protein Determination

The total protein amount was determined according to a Lawry method. A bovine serum albumin was used for forming a standard calibration curve.

(5) N-acetyl-D-glucosamine Determination

The N-acetyl-D-glucosamine content was determined according to a Morgan-Elson method.

(6) Glucosaminoglycan Determination

The sample was analyzed through colorimetry according to a 2-nitrophenylhydrazine coupling method. For standard calibration curve formation, comb-derived sodium hyaluronate (manufactured by Wako Pure Chemical Corporation, HARC) and *Streptococcus zooepidemicus*-derived sodium hyaluronate (manufactured by Wako Pure Chemical Corporation, HASZ) were used.

(7) Measurement of Molecular Weight of Low-Molecular Hyaluronic Acid

The molecular weight of hyaluronic acid was estimated through high-performance liquid chromatography (by Shimadzu Corporation) equipped with a differential refractometer (manufactured by Shimadzu Corporation, RID-10A Model). Columns of TSKgel G-2, 500PW$_{XL}$ (7.8 mm ID×30 cm) were used, and water was used as a mobile phase at a flow rate of 1 ml/min for analysis. As a molecular weight marker, four types of polyethylene glycol having a molecular weight of 400, 1000, 2000 or 6000 (manufactured by Aldrich Corp.) were used. The constituent weight ratio of each low-molecular hyaluronic acid was analyzed through high-performance liquid chromatography using samples of the nerve growth promoter or dextrin alone, in which the peak area of dextrin was detracted from the peak area of the nerve growth promoter to determine the constituent weight ratio.

[Component Analysis of Nerve Growth Promoter]

The produced nerve growth promoter 1' was analyzed for the constituent components thereof according to the above-mentioned method. The content of general components analyzed is shown in Table 1, the composition of free amino acids is shown in Table 2, and the analysis results of low-molecular hyaluronic acids are shown in Table 3. In Tables 1 to 3, "%" is "% by mass".

TABLE 1

| General Components | |
|---|---|
| | % |
| Water | 2.2-2.6 |
| Nitrogen | 3.84 |
| Total Protein | 3.04 |
| Free Amino Acid | 4.08 |
| N-acetylglucosamine | 0 |
| Dextrin (for food additive) | 75.0 |

TABLE 2

| Free Amino Acid Composition | |
|---|---|
| Amino Acid | Content % |
| p-serine | 1.71 |
| Taurine | 3.30 |
| Aspartic Acid* | 2.94 |
| Threonine* | 1.30 |
| Serine* | 2.20 |
| Glutamic Acid* | 2.18 |
| Glutamine | 0.48 |
| Sarcosine | 1.81 |
| Glycine* | 2.26 |
| Alanine* | 3.52 |
| Citrulline | 0.92 |
| α-Aminobutyric Acid | 2.18 |
| Cystine* | 1.03 |
| Methionine* | 1.97 |
| Cystine* | 2.78 |
| Leucine* | 2.26 |
| Isoleucine* | 6.27 |
| Tyrosine* | 2.65 |
| Phenylalanine* | 3.30 |
| β-aminoisobutyric Acid | 5.45 |
| Ornithine | 1.05 |
| Lysine* | 1.17 |
| 1-Methylhystidine | 0.78 |
| Anserine | 1.92 |
| Arginine* | 1.93 |
| Identified Total Amino Acids | 57.36 |
| Unknown Amino Acids | 42.64 |

*proteinogenic amino acids

TABLE 3

Estimated Molecular Weight, Constituent Unit Number and Constituent Weight Ratio of Low-Molecular HA

| Peak No. | 1 | 2 | 3 | 4 | 5 |
|---|---|---|---|---|---|
| Estimated Molecular Weight | 5,000 | 1,520 | 1,140 | 760 | 380 |
| Constituent Unit Number | 13-14 | 4 | 3 | 2 | 1 |
| Constituent Weight Ratio (%) | 33 | 47 | 10 | 6 | 4 |

As shown in Table 2, among the free amino acids contained in the nerve growth promoter 1', the content of isoleucine and p-aminoisobutyric acid was high, and then, alanine, taurine, phenylalanine, aspartic acid, cystine and tyrosine were contained much.

As shown in Table 3, the nerve growth promoter 1' contained five types of low-molecular hyaluronic acids each having an estimated molecular weight of 5000, 1520, 1140, 760 and 380. When the molecular weight of one recurring unit of hyaluronic acid is about 400, the recurring unit number of each low-molecular hyaluronic acid is 13 to 14, 4, 3, 2 and 1 in that order from the largest molecular weight, and the mass ratio was 33%, 47%, 10%, 6% and 4%. Accordingly, it is known that the main components of the low-molecular hyaluronic acids are two components of a 4-molecular component having a molecular weight of about 1520, and a 13 to 14-molecular component having a molecular weight of about 5000. The content of the low-molecular hyaluronic acids having a molecular weight of 380 to 5000 in the nerve growth promoter 1' was 13.4% by mass relative to the total amount of the nerve growth promoter 1'.

[Evaluation of Neurite Formation Promoting Effect]

(a) Evaluation of Dibutyryl cAMP-Induced Neurite Formation Promoting Effect

The nerve growth promoter 1 (freeze-dried powder of protease degradation product) produced in Production Example was evaluated for the dibutyryl cAMP-induced neurite formation promoting effect thereof. Evaluation samples were solutions prepared by dissolving the nerve growth promoter 1 in the liquid medium mentioned below at different concentrations.

The dibutyryl cAMP-induced neurite formation promoting effect was evaluated according to the method described in Biol. Pharm. Bull., 26, 341-346 (2003) using rat adrenal medullary pheochromocytoma-derived PC-12 cells.

First, in an RPMI-1640 medium (liquid medium) containing 10% HS (horse serum) and 5% FBS (fetal bovine serum), PC-12 cells were suspended to be $4.4 \times 10^4$ cells/mL to prepare a cell suspension. The cell suspension was sowed in a collagen-coated 96-well microplate at 90 μL/well, and then incubated in an air phase containing 5% $CO_2$ at 37° C. for 24 hours. After incubation, dibutyryl cAMP (dibutyryl cyclic adenosine monophosphate) was added to each well at a final concentration of 0.5 mM each, and 5 nL of the evaluation sample was added to each well. In 24 hours after the addition of dibutyryl cAMP and the evaluation sample, the medium was removed, and 100 μL of 1% glutaraldehyde was added to each well, and then statically kept as such for 20 minutes to fix the cells. Subsequently, glutaraldehyde was removed, and 100 μL of a Giemsa stain liquid was added to each well, and then statically kept as such for 20 minutes to stain each well. Subsequently, the Giemsa stain liquid was removed, and each well was washed twice with ultrapure water and then dried.

As in the above, the cells were fixed and stained, and then the length of 250 to 400 cells/well was measured. The cells having longer neurites than the major axis of each cell body were judged to be positive cells. The results of the percentage of the number of the positive cells to the total number of the measured cells (neurite formation rate) are shown in FIG. 1.

On the other hand, the same test as above was carried out except that, in place of dibutyryl cAMP, 5 μL of the liquid medium was added to each well where PC-12 cells were cultivated. The results are also shown in FIG. 1.

FIG. 1 is referred to. It is known that, in both systems added with or not added with dibutyryl cAMP, the neurite formation rate was increased by addition of the nerve growth promoter 1. This confirms that the nerve growth promoter 1 has an action of promoting formation and growth of neurites. However, in the system added with dibutyryl cAMP, the neurite formation rate increases depending on the concentration up to 0.3 μg/mL of the nerve growth promoter 1 in the medium, but when the concentration is more than 0.3 μg/mL, the neurite formation rate rather tends to lower. From this, it is known that the concentration of the nerve growth promoter 1 to be added to the medium is preferably 0.3 μg/mL or less.

(b) Evaluation of NGF-Induced Neurite Formation Promoting Effect

In actual living organisms, a nerve growth factor (NGF) plays roles of a neurite growth and neurotransmitter synthesis promoting effect, a nerve cell maintaining effect, a damaged cell repairing effect, and a cerebral nerve function recovering effect. Accordingly, here, in order to confirm the fact that the nerve growth promotor of the present invention could effectively act under the condition similar to that in a living organism, the NGF-induced neurite formation promoting effect was evaluated and, in addition, the formed neurites were investigated as to whether or not they were normally differentiated and induced. The evaluation samples are solutions prepared by dissolving the nerve growth promoter 1 in the above-mentioned liquid medium at different concentrations.

The evaluation of the NGF-induced neurite formation promoting effect was carried out in the same manner as that for the evaluation of the dibutyryl cAMP-induced neurite formation promoting effect mentioned above, except that the number of the PC-12 cells to be suspended in the medium was changed to $2.2 \times 10^4$ cells/mL, the nerve growth factor was added to each well in place of dibutyryl cAMP to have a final concentration of 10 ng/mL, the medium was removed in 48 hours after addition of NGF and the evaluation sample, and the cells were fixed with glutaraldehyde. The neurite formation rate of the cell group in each well was determined and the results are shown in FIG. 2.

As in FIG. 2, it is known that the NGF-induced neurite formation rate has the same concentration dependency as that of the dibutyryl cAMP-induced neurite formation rate shown in FIG. 1, and addition of the nerve growth promoter 1 brought about a significant neurite formation promoting effect in a low concentration range of 0.003 μg/mL or so.

In addition, the PC-12 cells on which NGF and the nerve growth promoter 1 had been acted were immunofluorescent-stained with a primary antibody (anti-neurofilament 200 IgG fraction of antiserum) and a secondary antibody (anti-rabbit IgG (whole molecule)-FITC antibody produced in goat), whereupon expression of neurofilaments of a differentiation marker was recognized.

This confirms that the nerve growth promoter 1 has an action of promoting NGF-induced neurite formation and can effectively contribute toward formation and growth of neurites in a living organism.

[Purification of Protease Degradation Product]

A freeze-dried powder of the protease degradation product prepared in the above-mentioned Production Example was purified as follows.

First, 32.0 g of a freeze-dried powder of the protease degradation product was filtered with ultrapure water added thereto, and the resulting filtrate was diluted with ultrapure water so as to have a total amount of 1.5 L. The diluted filtrate was processed twice for liquid-liquid separation with 1.5 L of ethyl acetate (EtOAc), and further the resultant aqueous fraction was processed twice for liquid-liquid separation with 750 ml of water-saturated 1-butanol. The water-saturated 1-butanol fraction, the ethyl acetate fraction and the aqueous fraction obtained in the liquid-liquid separation were evaluated for the dibutyryl cAMP-induced neurite formation promoting effect as mentioned above. The results are shown in FIG. 3. As in FIG. 3, the water-saturated 1-butanol fraction and the ethyl acetate fraction were recognized to have a high neurite formation promoting effect, and in particular, the water-saturated 1-butanol fraction was recognized to have a strong neurite formation promoting effect. In addition, the water-saturated 1-butanol fraction (solid content: 403.3 mg) and the aqueous fraction (solid content: 37.3 g) obtained in the liquid-liquid separation were purified through column chromatography in the manner mentioned below. The purification scheme is shown in FIG. 4. Of the columns in FIG. 4, the samples injected into the other columns than the columns 1 and 5 are, among the fractions each eluted from the column just before it, those recognized to have a relatively high activity in the dibutyryl cAMP-induced neurite formation promoting effect evaluation or a mixture of such fractions.

(a) Purification of Water-Saturated 1-Butanol Fraction

First, the water-saturated 1-butanol fraction was injected into the column 1 under the condition mentioned below, and eluted with 1 L of a flow of 70% methanol introduced thereinto.

(Condition of Column 1)
Column 1: TOYOPEARL HW-40C (diameter 4.0 cm×39.0 cm, 489.8 cm$^3$)
Sample: water-saturated 1-butanol fraction (solid content: 393.3 mg)
Fraction size: fraction 1, 100 mL; fractions 2 to 19, 50 mL
Eluent: 70% methanol (1 L)

The fraction 3 eluted from the column 1 was injected into the column 2 under the condition mentioned below, and eluted with 400 mL of a flow of 50% methanol introduced thereinto.

(Condition of Column 2)
Column 2: TOYOPEARL HW-40F (diameter 2.5 cm×length 37.8 cm, 185.5 cm$^3$)
Sample: fraction 3 from column 1 (solid content: 63.7 mg)
Flow rate: 1.2 mL/min
Fraction size: 10 mL
Eluent: 50% methanol (400 mL)

A mixture of the fractions 9 to 12 eluted from the column 2 was injected into the column 3 under the condition mentioned below, and eluted with 330 mL of a flow of 40% methanol introduced thereinto.

(Condition of Column 3)
Column 3: TOYOPEARL HW-40F (diameter 2.5 cm×length 34.2 cm, 167.8 cm$^3$)
Sample: mixture of fractions 9 to 12 from column 2 (solid content: 33.1 mg)
Flow rate: 1.2 mL/min
Fraction size: 10 mL
Eluent: 40% methanol (330 mL)

A mixture of the fractions 7 to 16 eluted from the column 3 was injected into the column 4 under the condition mentioned below, and eluted with 120 mL of a flow of 40% methanol introduced thereinto.

(Condition of Column 4)
Column 4: Sephadex LH-20 (diameter 1.5 cm×length 34.8 cm, 61.5 cm$^3$)
Sample: mixture of fractions 7 to 16 from column 3 (solid content: 22.2 mg)
Flow rate: 0.5 mL/min
Fraction size: 2.0 mL
Eluent: 40% methanol (120 mL)

A mixture of the fractions 12 to 15 (solid content: 12.1 mg) eluted from the column 4 was a nerve growth promoter 2.
(b) Purification of Aqueous Fraction The aqueous fraction was injected into the column 5 under the condition mentioned below, and eluted with methanol and water in such a manner that 5.0 L of a flow of the two was introduced thereinto in a blending ratio (methanol/water) of 0/100, 5/95, 10/90, 20/80 and 40/60 varied in that order.
(Condition of Column 5)
   Column 5: DIAION HP20 (diameter 12.0 cm×length 40.5 cm, 4578 cm$^3$)
   Sample: aqueous fraction (solid content: 37.3 g)
   Fraction size: 2.5 L
   Eluent: water, mixture of methanol and water The fractions 1 and 2 eluted from the column 5 were injected into the column 6 under the condition mentioned below, and eluted with methanol and water in such a manner that 2.0 L of a flow of the two was introduced thereinto in a blending ratio (methanol/water) of 0/100, 2.5/97.5 and 5/95 varied in that order.
(Condition of Column 6)
   Column 6: DIAION HP20 (diameter 7.0 cm×length 39.5 cm, 1519 cm$^3$)
   Sample: mixture of fractions 1 and 2 from column 5 (solid content: 4.8 g)
   Fraction size: 400 ml.
   Eluent: water, mixture of methanol and water A mixture of the fractions 2 to 6 eluted from the column 6 was injected into the column 7 under the condition mentioned below, and eluted with 2.05 L of a water flow introduced thereinto
(Condition of Column 7)
   Column 7: TOYOPEARL HW-40C (diameter 4.0 cm×length 41.5 cm, 521.2 cm$^3$)
   Sample: mixture of fractions 2 to 6 from column 6 (solid content: 3.5 g)
   Fraction size: 30 mL
   Eluent: water (2.05 L)

A mixture of the fractions 11 to 15 eluted from the column 7 was a nerve growth promoter 3.

The nerve growth promoters 2 and 3 purified according to the above-mentioned process were evaluated for the dibutyryl cAMP-induced neurite formation promoting effect as mentioned above, and the nerve growth promoters 2 and 3 were confirmed to have a higher neurite formation promoting effect than that of the nerve growth promoter 1.

Example 2: Antioxidant

The nerve growth promoter 1 produced in Production Example 1 was referred to as an antioxidant 1, and the nerve growth promoter 2 was referred to as an antioxidant 2, and these were evaluated as follows.
[Antioxidant Activity Evaluation]
(a) Radical Trapping Test The antioxidant 1 (freeze-dried powder of protease degradation product) produced was evaluated for the radical trapping activity against ABTS radical cations (unnatural model radical), according to the spectrophotometric method described in Biol. Pharm. Bull., 29, 766-771 (2006). Specifically, the antioxidant 1 was added to 3 mL of a reaction solution containing ABTS radical cations to be a final concentration of 300 µg/mL, and at the time after 5 minutes, 15 minutes, 30 minutes, 60 minutes and 120 minutes, the residual ratio of the ABTS radical cations was determined. For comparison, a system added with ascorbic acid or arbutin in an amount of 20 µM each in place of the antioxidant 1, and a system added with water in the same amount as that of the antioxidant 1 (control) were tested in the same manner. The results are shown in FIG. 5.

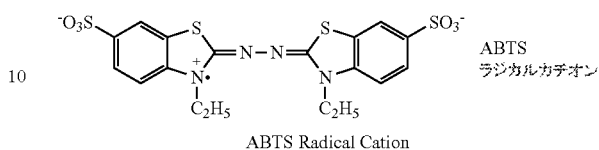

ABTS Radical Cation

From FIG. 5, it is known that, in the system added with the antioxidant 1, the residual ratio of the ABTS radical cations greatly reduced as compared with that in the control and in the system added with ascorbic acid, which confirms that the antioxidant 1 exhibits an excellent radical trapping activity. In addition, in the system added with ascorbic acid or arbutin, after the radical residual ratio reduced once, the radical residual ratio did not change after further lapse of time, but in the system added with the antioxidant 1, after the radical residual ratio greatly reduced once, the radical residual ratio still gradually reduced with the lapse of time. This confirms that the radical trapping activity of the antioxidant 1 is sustainable, which is a characteristic feature of an antioxidant.
(b) ORAC Method The antioxidant 1 (freeze-dried powder of protease degradation product) produced was evaluated for the antioxidant activity against alkoxy radicals and peroxy radicals generated from 2,2'-azobis(2-aminopropane) dihydrochloride (AAPH), according to the ORAC (oxygen radical absorbance capacity) method described in Biosci. Biotechnol. Biochem., 72, 1558-1563 (2008), in which a reaction solution was controlled to have a physical pH (pH 7.4) and evaluated. The amount of the antioxidant 1 used in the test was 30 µg/mL. For comparison, a system added with ascorbic acid in an amount of 3 µM in place of the antioxidant 1, and a system added with water in the same amount as that of the antioxidant 1 (control) were tested in the same manner. The results are shown in FIG. 6.

The ORAC method utilizes a phenomenon that fluorescein of a fluorescence probe is oxidized and decomposed by a radical and the fluorescence intensity thereof is thereby reduced, and it can be so evaluated that one capable of retarding the reduction in the fluorescence intensity (capable of shifting the graph to the right side) has a high antioxidant activity. The alkoxy radical and the peroxy radical used in this evaluation are radical species that simulate a lipid alkoxy radical and a lipid peroxy radical participating in peroxidation reaction of biogenic substances. Accordingly, the antioxidant activity evaluated here is considered to be approximate to the antioxidant activity in a living organism.

From the above-mentioned viewpoints, FIG. 6 is referred to. In this, the graph of the system added with the antioxidant 1 greatly shifts to the right side as compared with the graph of the control and the graph of the system added with ascorbic acid, which shows that the reduction in the fluorescence intensity from the system added with the antioxidant 1 is retarded. This suggests that the antioxidant 1 can exhibit a higher antioxidant activity than ascorbic acid in peroxidation reaction of biogenic substances.

(c) Oxystress-Induced Erythrocyte Hemolysis Inhibition Test

The antioxidant 1 (freeze-dried powder of protease degradation product) produced was evaluated for the antioxidant activity against alkoxy radicals and peroxy radicals generated from 2,2'-azobis(2-aminopropane) dihydrochloride (AAPH), according to the oxystress-induced erythrocyte hemolysis inhibition test described in Food Chem., 134, 606-610 (2012). The amount of the antioxidant 1 used in the test was 300 µg/mL. For comparison, a system added with ascorbic acid in an amount of 50 µM in place of the antioxidant 1, and a system added with water in the same amount as that of the antioxidant 1 (control) were tested in the same manner. The tests were repeated three times under the same condition, and the results of the average data and the standard deviation are shown in FIG. 7.

The oxystress-induced erythrocyte hemolysis inhibition test utilizes a phenomenon that the erythrocyte residual ratio reduces owing to the hemolysis (oxygenation failure) caused by oxidation of lipids and proteins in erythrocyte membranes by alkoxy radicals and peroxy radicals, and it can be so evaluated that one capable of retarding the hemolysis (capable of shifting the graph to the right side) has a high antioxidant activity.

FIG. 7 is referred to. In this, the graph of the system added with the antioxidant 1 shifts to the right side as compared with the graph of the control and the graph of the system added with ascorbic acid, which shows more retardation of erythrocyte hemolysis. This confirms that the antioxidant 1 has an effect of effectively inhibit oxygenation failure in a living organism, and the effect is greatly higher than that of ascorbic acid.

[Purification of Protease Degradation Product]

The freeze-dried powder of the protease degradation product prepared in Production Example in Example 1 was purified as follows.

First, 32.0 g of the freeze-dried powder of the protease degradation product was filtered with ultrapure water added thereto, and the resulting filtrate was diluted with ultrapure water so as to have a total amount of 1.5 L. The diluted filtrate was processed twice for liquid-liquid separation with 1.5 L of ethyl acetate (EtOAc), and further the resultant aqueous fraction was processed twice for liquid-liquid separation with 750 ml of water-saturated 1-butanol. The water-saturated 1-butanol fraction, the ethyl acetate fraction and the aqueous fraction obtained in the liquid-liquid separation were tested in the radical trapping test using ABTS radical cations mentioned above. The results are shown in FIG. 8. As in FIG. 8, the water-saturated 1-butanol fraction and the aqueous fraction were recognized to have a high antioxidant effect, and in particular, the water-saturated 1-butanol fraction was recognized to have a strong antioxidant effect. In addition, the water-saturated 1-butanol fraction (solid content: 403.3 mg) and the aqueous fraction (solid content: 37.3 g) obtained in the liquid-liquid separation were purified through column chromatography in the manner mentioned below. The purification scheme is shown in FIG. 9. Of the columns in FIG. 9, the samples injected into the other columns than the columns 1 and 5 are, among the fractions each eluted from the column just before it, those recognized to have a relatively high activity in the radical trapping test using ABTS radical cations or a mixture of such fractions.

(a) Purification of Water-Saturated 1-Butanol Fraction

First, the water-saturated 1-butanol fraction was injected into the column 1 under the condition mentioned below, and eluted with 1 L of a flow of 70% methanol introduced thereinto.

(Condition of Column 1)
Column 1: TOYOPEARL HW-40C (diameter 4.0 cm×39.0 cm, 489.8 cm$^3$)
Sample: water-saturated 1-butanol fraction (solid content: 393.3 mg)
Fraction size: fraction 1, 100 mL; fractions 2 to 19, 50 mL
Eluent: 70% methanol (1 L)

The fraction 4 eluted from the column 1 was injected into the column 2 under the condition mentioned below, and eluted with 400 mL of a flow of 50% methanol introduced thereinto.

(Condition of Column 2)
Column 2: TOYOPEARL HW-40F (diameter 2.5 cm×length 35.0 cm, 171.7 cm$^3$)
Sample: fraction 4 from column 1 (127.0 mg)
Flow rate: 1.2 mL/min
Fraction size: 10 mL
Eluent: 50% methanol (400 mL)

A mixture of the fractions 13 and 14 eluted from the column 2 was injected into the column 3 under the condition mentioned below, and eluted with 400 mL of a flow of 40% methanol introduced thereinto.

(Condition of Column 3)
Column 3: TOYOPEARL HW-40F (diameter 2.5 cm×length 34.5 cm, 170.0 cm$^3$)
Sample: mixture of fractions 13 and 14 from column 2 (solid content: 47.8 mg)
Flow rate: 1.0 mL/min
Fraction size: 10 mL
Eluent: 40% methanol (400 mL)

The fraction 13 eluted from the column 3 was injected into the column 4 under the condition mentioned below, and eluted with 80 mL of a flow of 50% methanol introduced thereinto.

(Condition of Column 4)
Column 4: Sephadex LH-20 (diameter 1.0 cm×length 26.0 cm, 20.41 cm$^3$)
Sample: fraction 13 from column 3 (solid content: 14.2 mg)
Flow rate: 0.5 mL/min
Fraction size: 2.0 mL
Eluent: 50% methanol (80 mL)

A mixture of the fractions 7 to 11 eluted from the column 4 was an antioxidant 2.

(b) Purification of Aqueous Fraction

The aqueous fraction was injected into the column 5 under the condition mentioned below, and eluted with methanol and water in such a manner that 5.0 L of a flow of the two was introduced thereinto in a blending ratio (methanol/water) of 0/100, 5/95, 10/90, 20/80 and 40/60 varied in that order.

(Condition of Column 5)
Column 5: DIAON HP20 (diameter 12.0 cm×length 40.5 cm, 4578 cm$^3$)
Sample: aqueous fraction (solid content: 37.3 g)
Fraction size: 2.5 L
Eluent: water, mixture of methanol and water A mixture of the fractions 7 to 12 eluted from the column 5 was injected into the column 6 under the condition mentioned below, and eluted with methanol and water in such a manner that 4.0 L of a flow of the two was introduced thereinto in a blending ratio (methanol/water) of 0/10, 1/9, 2/8, 4/6, 6/4 and 8/2 varied in that order.

(Condition of Column 6)
  Column 6: DIAION HP20 (diameter 12.0 cm×length 40.5 cm, 4578 cm$^3$)
  Sample: mixture of fractions 7 to 12 from column 5 (solid content: 12.58 g)
  Fraction size: 2.0 L
  Eluent: water, mixture of methanol and water A mixture of the fractions 8 and 9 eluted from the column 6 was injected into the column 7 under the condition mentioned below, and eluted with methanol and water in such a manner that 2.0 L of a flow of the two was introduced thereinto in a blending ratio (methanol/water) of 0/10, 1/9, 2/8, 3/7, 4/6, 5/5 and 6/4 varied in that order.

(Condition of Column 7)
  Column 7: DIAION HP20 (diameter 7.0 cm×length 36.5 cm, 1404 cm$^3$)
  Sample: mixture of fractions 8 and 9 from column 6 (solid content: 6.57 g)
  Fraction size: 500 mL
  Eluent: water, mixture of water and methanol A mixture of the fractions 21 to 26 eluted from the column 7 was injected into the column 8 under the condition mentioned below, and eluted with a flow of 1.0 L of 50% methanol introduced thereinto.

(Condition of Column 8)
  Column 8: TOYOPEARL HW-40C (diameter 4.0 cm×length 43 cm, 540.0 cm$^3$)
  Sample: mixture of fractions 21 to 26 from column 7 (solid content: 2.0 g)
  Fraction size: 30 mL
  Eluent: 50% methanol (1.0 L)

A mixture of the fractions 13 and 14 eluted from the column 8 was an antioxidant 3.

The antioxidants 2 and 3 purified according to the above-mentioned process were tested according to the radical trapping test, the ORAC test and the oxystress-induced erythrocyte hemolysis inhibition test as mentioned above. As a result, it was confirmed that the antioxidants 2 and 3 have a higher antioxidant activity than the antioxidant 1. Among the fractions obtained in the liquid-liquid separation, the water-saturated 1-butanol fraction has a high antioxidant activity, and further, the antioxidant 2 obtained by purifying the water-saturated 1-butanol fraction has an extremely high antioxidant activity.

Example 3: Wound Treatment Agent

Production Example 32.0 g of the nerve growth promoter 1' (dextrin-added freeze-dried powder) produced in Production Example in Example 1 was filtered with ultrapure water added thereto, and the resultant filtrate was diluted with ultrapure water to have a total amount of 1.5 L. The dilution of the filtrate was processed for liquid-liquid separation twice with 1.5 L of ethyl acetate (EtOAc) to give an aqueous fraction and an ethyl acetate fraction. Among these, the ethyl acetate fraction was collected to be a wound treatment agent 1.

On the other hand, 750 ml of water-saturated 1-butanol was added to the aqueous fraction for liquid-liquid separation, and the operation was repeated twice to give an aqueous fraction and a water-saturated 1-butanol fraction.

[Evaluation of Wound Healing Promoting Effect]

The wound treatment agent 1 (ethyl acetate fraction (EtOAc fraction) of protease degradation product), the freeze-dried powder of the protease degradation product, and for comparison, the aqueous fraction and the water-saturated 1-butanol fraction (water-saturated 1-BuOH fraction) of the protease degradation product were evaluated for the wound healing curing effect. The evaluation samples were prepared to have a different solid concentration as in FIG. 11.

Using human skin fibroblasts (NB1RGB cells) and normal human skin fibroblasts (CSC2F0 cells), the samples were evaluated for the wound healing promoting effect as follows.

First, NB1RGB cells or CSC2F0 cells were suspended in a 10% FBS/DMEM medium to be 6.0×10$^4$ cells/mL, and the suspension was sowed in a 24-well plate in an amount of 1.0 mL/well, and then cultivated in an air phase containing 5% $CO_2$ at 37° C. for 24 hours. As shown in FIG. 10(a), after the cultivation, the center part of the well 12 was scratched from the top downward, using a self-scratcher 11, to make a 2-mm wide scratch. The medium was removed by suction, and after once washing with a basal medium, a fresh serum-free DMEM was added to each well in an amount of 900 μl/well, and further the evaluation sample having a different concentration was added to each well in an amount of 100 μL/well. In 48 hours after the addition of the evaluation sample, the medium was removed, and 1% glutaraldehyde was added to each well in an amount of 500 μL/well, and statically left as such for 20 minutes to fix the cells. Subsequently, glutaraldehyde was removed, and a Giemsa stain was added to each well in an amount of 500 μL/well, and statically left as such for 20 minutes for staining. Subsequently, the Giemsa stain was removed, and each well was washed once with ultrapure water and dried. In the cell group in each well thus stained in the manner as above, as shown in FIG. 10(b), the position to which 5 or more cells 2 migrated on a line was considered to be a longest migration point, and a length calculated by subtracting the length A between the longest migration points (width of the wounded part) from the width 2 mm of the scratch 1 that had been made by the self-scratcher, 2-A (mm) was referred to as a cell migration distance. The results of the cell migration distance measured in the cell group added with the evaluation sample are shown in FIG. 11. In FIG. 11, "control" is a result of wound healing promoting effect evaluation made in the same manner as above except that the evaluation sample was not added.

As shown in FIG. 11, the cell migration distance in the control was about 0.7 mm, while in the system added with the wound treatment agent (ethyl acetate fraction), the cell migration distance was about 1.6 mm and was extremely long when the concentration of the wound treatment agent added was 12.5 μg/mL. In the system added with the freeze-dried powder of the protease degradation product as it was, the cell migration distance at a concentration of 250 μg/mL was about 1.2 mm, and as compared with this, the wound treatment agent 1 attained the above-mentioned long cell migration distance at a concentration of 1/10 or less of the concentration of the freeze-dried powder. In addition, also in the system added with the water-saturated 1-butanol fraction or the aqueous fraction, the cell migration distance became long as compared with that in the control, but in these systems, the cell migration distance was short though the concentration of the fraction added was high as compared with that in the system added with the ethyl acetate fraction. These suggest that the component to promote wound healing contained in the protease degradation product may dominantly transfer to the ethyl acetate fraction, and confirm that the ethyl acetate fraction (wound treatment agent) has a much more excellent wound healing promoting effect than the protease degradation product itself or than the aqueous fraction and the water-saturated 1-butanol fraction.

[Purification of Protease Degradation Product]

The ethyl acetate fraction (solid content: 176.8 mg) obtained in the above-mentioned Production Example and the aqueous fraction (solid content: 37.3 g) obtained for comparison were purified through column chromatography as follows. The purification scheme is shown in FIG. 12. Of the columns in FIG. 12, the samples injected into the other columns than the columns 1 and 3 are, among the fractions each eluted from the column just before it, those recognized to have a relatively high activity for the wound healing promoting effect according to the above-mentioned evaluation method or a mixture of such fractions.

(a) Purification of Ethyl Acetate Fraction

The ethyl acetate fraction was injected into the column 1 under the condition mentioned below, then 100 mL of a mixture flow of toluene and acetone was introduced into the column 1 in a blending ratio (toluene/acetone) of 10/0, 9/1, 8/2 and 6/4 varied in that order, then 200 mL of an acetone flow was introduced into the column, and thereafter 200 L of a mixture flow of acetone and methanol mixed in a blending ratio (acetone/methanol) of 9/1 was introduced into the column 1 for elution.

(Condition of Column 1)
  Column 1: Wakogel C-200 (diameter 2.0 cm×length 13 cm, 40.8 cm$^3$)
  Sample: ethyl acetate fraction (solid content: 177 mg)
  Fraction size: fractions 1 to 25, 20 mL; fraction 26, 50 mL; fractions 27 and 28, 100 mL
  Eluent: toluene, mixture of toluene and acetone, acetone and mixture of acetone and methanol A mixture of the fractions 8 and 9 eluted from the column 1 was injected into the column 2 under the condition mentioned below, then 25 mL of a mixture flow of hexane and ethyl acetate was introduced into the column 2 in a blending ratio (hexane/ethyl acetate) of 10/0, 9/1, 8/2, 6/4 (one drop of acetic acid was added to each mixture) varied in that order, and then 50 mL of a mixture flow of hexane and ethyl acetate mixed in a blending ratio (hexane/ethyl acetate) of 4/6 (one drop of acetic acid was added to the mixture) was introduced thereinto for elution.

(Condition of Column 2)
  Column 2: Wakogel C-300 (diameter 1.0 cm×length 28.0 cm, 22.0 cm$^3$)
  Sample: mixture of fractions 8 and 9 from column 1 (89.0 mg)
  Fraction size: 2.5 mL
  Eluent: hexane, mixture of hexane and ethyl acetate added with one drop of acetic acid A mixture of the fractions 1 to 20 eluted from the column 2 was a wound treatment agent 2.

(b) Purification of Aqueous Fraction

The aqueous fraction was injected into the column 3 under the condition mentioned below, and 5.0 L of a mixture flow of methanol and water was introduced into the column 3 in a blending ratio (methanol/water) of 0/100, 5/95, 10/90, 20/80 and 40/60 varied in that order for elution.

(Condition of Column 3)
  Column 3: DIAION HP20 (diameter 12.0 cm×length 40.5 cm, 4578 cm$^3$)
  Sample: aqueous fraction (solid content: 37.3 g)
  Fraction size: 2.5 L
  Eluent: water, mixture of methanol and water A mixture of the fractions 5 and 6 eluted from the column 3 was injected into the column 4 under the condition mentioned below, and 2 L of a mixture flow of methanol and water was introduced into the column 4 in a blending ratio (methanol/water) of 0/100, 2.5/97.5, 5/95, 10/90 and 15/85 varied in that order for elution.

(Condition of Column 4)
  Column 4: DIAION HP20 (diameter 7.0 cm×length 43 cm, 1654 cm$^3$)
  Sample: mixture of fractions 5 and 6 from column 3 (solid content: 5.1 g)
  Fraction size: 500 mL
  Eluent: water, mixture of methanol and water A mixture of the fractions 8 to 10 eluted from the column 4 was injected into the column 5 under the condition mentioned below, and eluted with 1.5 L of a water flow introduced thereinto.

(Condition of Column 5)
  Column 5: TOYOPEARL HW-40C (diameter 4.0 cm×length 35 cm, 440 cm$^3$)
  Sample: mixture of fractions 8 to 10 from column 4 (solid content: 509.4 mg)
  Fraction size: 30 mL
  Eluent: water (1.5 L)

A mixture of the fractions 14 to 18 eluted from the column 5 was a purified aqueous fraction.

The wound treatment agent 2 purified in the above-mentioned process was evaluated for the wound healing promoting effect according to the same method as above, and was confirmed to have a higher wound healing promoting effect than the wound treatment agent 1 and the purified aqueous fraction.

INDUSTRIAL APPLICABILITY

According to the present invention, there can be provided a nerve growth promoter at low cost, which can effectively promote formation and growth of neurites in nerve cells. Accordingly, using the nerve growth promoter of the present invention, there can be provided an inexpensive internal preparation capable of relieving cognitive dysfunction and motor dysfunction caused by neurodegenerative disorders of nerve damages. In addition, according to the present invention, there can be provided an antioxidant at low cost, which has a high antioxidant activity and can effectively prevent oxygenation failures of a living organism. Consequently, using the antioxidant of the present invention can prevent increase in active oxygen-caused aging and can prevent onset of various disorders such as typically lifestyle-related diseases. Further, there can be provided an inexpensive internal preparation or external preparation having a high antioxidant activity. In addition, according to the present invention, there can be provided a wound treatment agent at low cost, which can noticeably promote wound healing and can exhibit a high wound treatment effect. Consequently, using the wound treatment agent of the present invention can rapidly heal wounds and can provide an inexpensive internal preparation or external preparation having a high would treatment effect. Accordingly, the industrial applicability of the present invention is great.

The invention claimed is:

1. A method for promoting nerve growth, comprising administering to a subject in need thereof an ethyl acetate fraction, as a nerve growth promoting agent, obtained by degrading a chicken's comb containing a hyaluronic acid and a protein with a protease followed by extracting with ethyl acetate to produce an aqueous fraction and the ethyl acetate fraction.

2. The method for treating a wound according to claim 1, wherein the chicken's comb is a rooster's comb.

\* \* \* \* \*